United States Patent
Mohr et al.

(10) Patent No.: US 11,549,910 B2
(45) Date of Patent: Jan. 10, 2023

(54) METHOD FOR MEASURING MULTIPLE PARAMETERS OF DRILLING FLUID

(71) Applicant: Mohr and Associates, Richland, WA (US)

(72) Inventors: Charles L. Mohr, Richland, WA (US); Brandt C. Mohr, Richland, WA (US); Benno Mohr, Richland, WA (US); Michael Stordahl, Kennewick, WA (US); James Van Corbach, Sunnyside, WA (US); Erik Von Reis, Kennewick, WA (US); Christopher Mulkey, West Richland, WA (US); Ryan Sams, Kennewick, WA (US); Kevin Dawes, Richland, WA (US); Preston May, Richland, WA (US); Duan Nguyen, Pasco, WA (US); Gordon Anderson, Benton City, WA (US); Dan Kenney, Richland, WA (US); Bill Rausch, Richland, WA (US); David Hurley, Pasco, WA (US)

(73) Assignee: Mohr and Associates, Richland, WA (US)

( * ) Notice: Subject to any disclaimer, the term of this patent is extended or adjusted under 35 U.S.C. 154(b) by 455 days.

(21) Appl. No.: 16/615,078

(22) PCT Filed: May 9, 2018

(86) PCT No.: PCT/US2018/031738
§ 371 (c)(1),
(2) Date: Nov. 19, 2019

(87) PCT Pub. No.: WO2018/217450
PCT Pub. Date: Nov. 29, 2018

(65) Prior Publication Data
US 2020/0166478 A1    May 28, 2020

Related U.S. Application Data

(60) Provisional application No. 62/509,080, filed on May 20, 2017.

(51) Int. Cl.
*G01N 27/74*    (2006.01)
*G01K 13/02*    (2021.01)
(Continued)

(52) U.S. Cl.
CPC ............. *G01N 27/74* (2013.01); *E21B 21/00* (2013.01); *G01K 13/02* (2013.01); *G01N 9/26* (2013.01);
(Continued)

(58) Field of Classification Search
CPC ...... G01N 27/74; G01N 9/26; G01N 33/2823; G01N 33/2847; E21B 21/00; G01K 13/02
(Continued)

(56) References Cited

U.S. PATENT DOCUMENTS

| 4,786,857 A | 11/1988 | Mohr et al. |
| 5,723,979 A | 3/1998 | Mohr |

(Continued)

OTHER PUBLICATIONS

Notification of Transmittal of the International Search Report and the Written Opinion of the International Searching Authority, or the Declaration, PCY/US18/31738, dated Aug. 30, 2018.
(Continued)

*Primary Examiner* — Nimeshkumar D Patel
*Assistant Examiner* — Jean F Morello
(74) *Attorney, Agent, or Firm* — Randall Danskin P.S.

(57) ABSTRACT

A method and apparatus for measuring multiple parameters of drilling fluid using electric field perturbation, permittivity curves, time domain analysis and frequency domain analysis to identify constituents of drilling fluid and ratios of the drilling fluid constituents on a real time basis and to measure volumes and densities of the constituents on a real time basis.

14 Claims, 21 Drawing Sheets

(51) Int. Cl.
*G01N 9/26* (2006.01)
*G01N 33/28* (2006.01)
*E21B 21/00* (2006.01)

(52) U.S. Cl.
CPC ..... *G01N 33/2823* (2013.01); *G01N 33/2847* (2013.01); *G01K 13/026* (2021.01)

(58) Field of Classification Search
USPC .......................................................... 702/50
See application file for complete search history.

(56) References Cited

U.S. PATENT DOCUMENTS

| | | |
|---|---|---|
| 6,144,211 A | 11/2000 | Mohr |
| 6,348,803 B1 | 2/2002 | Mohr |
| 10,048,219 B2 | 8/2018 | Mohr et al. |
| 10,119,850 B2 | 11/2018 | Mohr et al. |
| 10,119,929 B2 | 11/2018 | Mohr et al. |
| 2005/0000289 A1 | 1/2005 | Gysling et al. |
| 2014/0085133 A1 | 3/2014 | Flasza et al. |

OTHER PUBLICATIONS

Communication Pursuant to Article 94 (3) EPC (office action) from the European Patent Office dated Oct. 25, 2021.
Extended European Search Report dated Apr. 16, 2021.

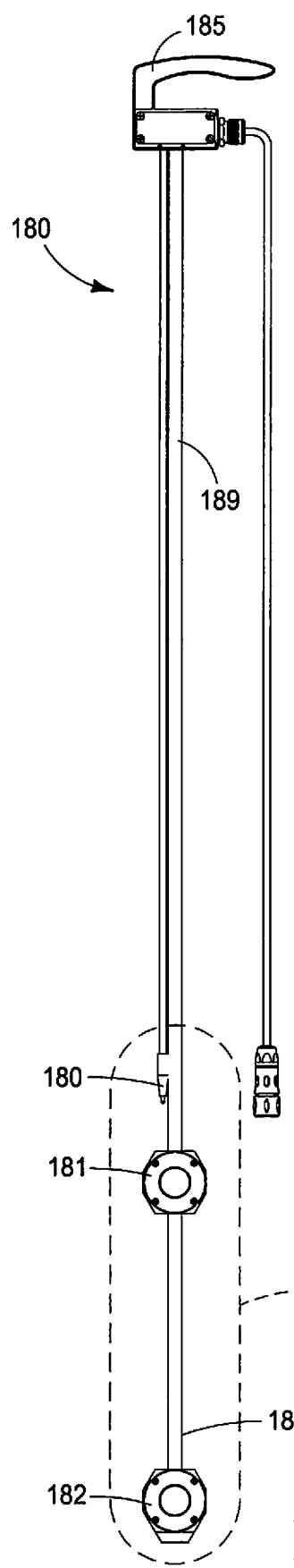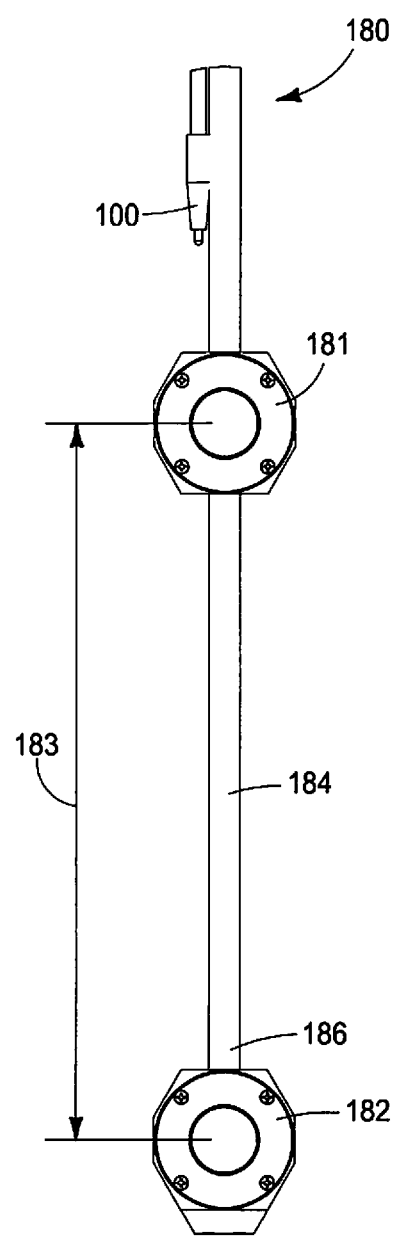
FIG. 5
FIG. 6

METHOD FOR MEASURING MULTIPLE PARAMETERS OF DRILLING FLUID

RELATED APPLICATIONS

Technical Field

This invention relates to a method for measuring multiple parameters of drilling fluid during drilling operations, and more specifically to a method using electric field perturbation and permittivity curves to measure volume fractions of water and oil in drilling fluid and for determining water/oil ratios and densities of drilling fluid.

BACKGROUND OF THE INVENTION

Drilling fluid is a complex oil-based or aqueous-based mixture of synthetic and organic compounds which is expensive and frequently proprietary in nature.

In the drilling of a petroleum well, drilling fluids are continually pumped, at high pressure, into the upper end of the drill-string whereupon the drilling fluid is forced downwardly through the drill-string and outwardly through a cutter head at the bottom of the wellbore. The continuous supply of drilling fluid at high pressure exiting the cutter head forces the drilling fluid, and cuttings and debris carried within the drilling fluid within the wellbore, and external to the drill string, to move upwardly between the circumferential wall of the wellbore and the outer circumferential surface of the drill string, and to be regurgitated from the bore hole at the surface. Drilling fluid is critical to the drilling operation and the drilling fluid performs several simultaneous functions. The drilling fluid lubricates the cutter head and dissipates heat. The drilling fluid also evacuates "cuttings" and rock chips from the wellbore. Further, the drilling fluid seals and stabilizes the circumferential walls of the wellbore to prevent leakage, collapse, "kicks" and "blow-outs".

Drilling operations expose the drilling fluid to ground water and thus the drilling fluid can become diluted by the water encountered in the drilling process. If a well passes into, or penetrates, a significant quantity of water, the ratio of the drilling fluid constituents, such as oil to water, will change significantly and the density of the drilling fluid will consequently be reduced. The density of the drilling fluid is an integral component of drilling operations and is an important parameter to maintain safety and preventing accidents and control of the drilling process.

The instant method and apparatus measures the density of the drilling fluid, corrected for temperature, as well as the ratio of oil and water in an oil-based drilling fluid as well as the water fraction in water-based drilling fluids. The method and apparatus herein has a central instrument package and two probes, one for measurement of the oil/water ratio and measures of temperature, and a second probe that measures temperature and density provided by a differential pressure between two pressure transducers spaced apart by a known distance, corrected for temperature. The disclosed method uses electric field perturbation (EFP) to perform the measurements.

Large tanks or pits are used to mix, store, filter and recirculate the drilling fluid during drilling operations. Typically, the last step of storage and mixing of the drilling fluid is a suction tank from which the drilling fluid is suctioned and then pumped to the top of the drill string by pumps, and injected downwardly into the well through the drill string. The injected drilling fluid displaces the drilling fluid within the wellbore that is carrying drilling cuttings and debris which is circulated upwardly back to the surface where the "regurgitated" drilling fluid is dispersed onto a shaker table which removes large cuttings and debris from the fluid. Following the shaker table, the fluid is moved to settling tanks where some percentage of the fluid is transferred to a centrifuge to remove the majority of smaller cuttings, sand and debris, and then the fluid is re-mixed with return fluid for pumping back into the wellbore to continue the drilling operation.

The primary safety assessment tools in a drilling operation include correlating the volume of drilling fluid returning "out of the wellbore" (called "return fluid") with the volume of "fresh" drilling fluid being injected back into the wellbore; the density of the return fluid; and the density of the "fresh" drilling fluid being pumped back down the wellbore. Determination of the oil/water fraction of the drilling fluid provides a measure of the dilution of the drilling fluid, and that determination/measure, when combined with a measurement of the density of the return fluid and the density of the fresh drilling fluid, forms the basis for the safety assessment of the operation of the well and the drilling operation. These measures allow an operator/driller to determine what materials/additives may need to be added to the drilling fluid, during the drilling operation to maintain a desired drilling fluid density that is capable of evacuating cuttings from the wellbore to prevent loss of the cutter head, and sealing the circumferential surfaces of the well bore to prevent "kicks" and "blow-outs" as well as the fluid chemistry so as to maintain safety of the drilling operation.

During circulation in the wellbore, the drilling fluid can become diluted with groundwater and other liquids, or altered chemically by naturally occurring substances. Continual monitoring of the drilling fluid is essential to the successful completion of a well drilling operation as it prevents "binding" of the drill bit, removes "cuttings" and prevents "kicks" or "blowouts" of the well. During the "kick" or "blowout", the possibility of explosion and fire is high which can be deadly to workers and cause extensive damage to drilling equipment.

The instant inventive method and apparatus is used to measure and characterize multiple "in situ", real-time parameters of drilling fluid including, but not limited to, density, temperature, volume fraction of water, volume fraction of oil and the oil/water ratio. The instant measuring method provides a near real-time measurement of these parameters which are directly related to drilling safety. The apparatus may be portable or may also be a fixed part of a drilling process and plumbed into the fluid system of the drilling rig.

Another important measurement problem in the oil and hydrocarbon production industry is the accurate measurement of water content. Water content directly affects the price paid for the product. Various devices are available to continuously measure water content, and most such devices are capacitance meters which measure the dielectric constant of the oil/water mixture to determine the water content. Unfortunately, such devices, which are known in the industry as "water cut meters" are not continuously accurate because the temperature, density and dielectric constant of the oil/water mixture all change as measurement conditions change, which results in measurement errors.

A further complicating factor in measuring volume fraction constituents of mixtures of produced oil and water is the salt content of the mixture because salt affects the dielectric constant of the fluid components. Similarly, lubricants within the drilling mud and proprietary lubricating drilling fluids may further affect the dielectric constants of the components which may make accurate identification and measurements difficult.

The instant Electric Field Perturbation (EFP) Drilling Fluid Measurement System provides rapid assessment of the density and composition of the fluid used in drilling oil wells. Currently there many types of drilling fluids used in a well drilling operations. The primary types of drilling fluids are water based fluids and oil based fluids due to cost and ease of handling. Injecting drilling fluid down into the bore hole exposes the drilling fluid to additional dilution with water and thus the oil based fluids which are made with a small fraction of water are then diluted by the water encountered in the drilling process. If a well intersects a significant quantity of water the ratio of oil to water will change significantly and the density will be reduced. A similar situation occurs with water based fluids that undergo dilution of the fluid by coming in contact with a significant quantity of water which again changes the density of the fluid mixture. The density of the fluid, as part of the oil well exploration and drilling operation, is a very important parameter in maintaining safety and preventing accidents and control of the drilling process. The measurement of the Oil/Water ratio in oil based fluids as well as the actual water content in the water based drilling fluid is an important safety parameter. The instant EFP system can measure the density, corrected for temperature, and the ratio of oil and water in the oil based drilling fluid. The instant method can also measure the water fraction in the water based fluids. The system described herein consists of a central instrument package and two probes, one probe for measurement of the oil/water ratio, and the second probe that measures temperature and fluid density provided by the differential pressure between two pressure transducers and temperature of the probe inserted into the fluid mixture. The method uses the Electric Field Perturbation (EFP) technique to measure the oil and water for oil based fluid or the water content for the water based drilling fluids.

Our method and apparatus for measuring multiple parameters of drilling fluid overcomes various of the drawbacks of known identifying and measuring methods and apparatus.

SUMMARY OF THE INVENTION

A first aspect of the present invention is a method for measuring multiple parameters of fluid comprising providing a source of fluid having a volume fraction of water and a volume fraction of oil, and wherein the volume fraction of water and the volume fraction of oil each have a previously determined and known complex permittivity curve; providing a database having stored accessible information about the previously determined and known complex permittivity curves of water and of oil; providing a temperature probe exposed to the fluid to determine the temperature of the fluid; providing an Electric Field Perturbation (EFP) probe exposed to the fluid, and wherein the EFP probe has a known length; providing an electrical pulse emitter that electronically generates an electrical pulse and which is delivered to the EFP probe, and wherein the electrical pulse travels the known length of the EFP probe, and subsequently generates an electrical pulse reflection; providing an electrical pulse sampler electronically coupled with the EFP probe, and which further receives, and senses, the electrical pulse reflection generated by electrical pulse, and which further receives, and senses, the electrical pulse transmitted through the EFP probe; providing a controller/computer electronically coupled with the temperature probe, the EFP probe, the electrical pulse emitter, the electrical pulse sampler, and the database, and wherein the controller/computer determines a time period between the electrical pulse emission into the EFP probe, and the receipt of the sensed electrical pulse reflection from the EFP probe, and wherein resonance points of the fluid are calculated by the controller/computer from the electrical pulse reflection and transmission by applying a Fast Fourier Transform (FFT) algorithm to the electrical pulse reflection and transmission, and wherein scattering parameters S11 and S21 are calculated by the controller/computer from the electrical pulse reflection and transmission by applying a Fast Fourier Transform (FFT) algorithm to the electrical pulse reflection and transmission, and wherein the complex permittivity curve of the fluid oil and water mixture is calculated by the controller/computer from the scattering parameters S11 and S21, and wherein the controller/computer further correlates the determined time period and the determined resonance points and the calculated complex permittivity curve to the previously determined, and known, complex permittivity curves of the volume fraction of water, and the volume fraction of oil, as provided in the database, and as adjusted for temperature to identify the volume fraction of water, and the volume fraction of oil in the fluid thereby allowing the controller/computer to determine an oil/water ratio of the fluid; providing a density probe having an elongate support with a handle end, and an opposing distal end, and wherein the elongate support carries a first pressure transducer which is located proximate to the handle end and which is exposed to the fluid, and a second pressure transducer is located at the distal end, opposite the handle, and is simultaneously exposed to the fluid, and wherein a known predetermined distance is established between the first pressure transducer, and the second pressure transducer; operationally coupling the controller/computer with the first pressure transducer and with the second pressure transducer, and determining a pressure differential between the first pressure transducer and the second pressure transducer so as to calculate the density of the fluid based upon the identified volume fraction of water, and the identified volume fraction of oil as adjusted for temperature as previously provided by the temperature probe; and providing a user interface visual display electronically coupled with the controller/computer, and which receives the determined measurement of the oil water ratio, and the density of the fluid, and which further generates a user perceivable output which identifies the oil water ratio and the density of the fluid.

A second aspect of the present invention is a method for measuring multiple parameters of fluid comprising providing a source of fluid having a volume fraction of water and a volume fraction of oil, and wherein the volume fractions of water and of oil each have a previously determined and known complex permittivity curve; providing a database having stored accessible information about the previously determined and known complex permittivity curve of the volume fractions of water and of oil; providing a temperature probe exposed to the fluid to determine the temperature of the fluid; providing an Electric Field Perturbation (EFP) probe exposed to the fluid, and wherein the EFP probe has a known length; providing an electrical pulse emitter that electronically generates an electrical pulse and which is delivered to the EFP probe, and wherein the electrical pulse travels the known length of the EFP probe, and subsequently generates an electrical pulse reflection; providing an electrical pulse sampler electronically coupled with the EFP probe, and which further receives, and senses, the electrical pulse reflection generated by electrical pulse within the EFP probe; providing a controller/computer electronically coupled with the temperature probe, the EFP probe, the electrical pulse emitter, the electrical pulse sampler, and the database, and wherein the controller/computer determines a time period between the electrical pulse emission into the EFP probe, and the receipt of the sensed electrical pulse reflection from the EFP probe, and wherein resonance points of the fluid are calculated by the controller/computer from the electrical pulse reflection by applying a Fast Fourier Transform (FFT) algorithm to the electrical pulse reflection, and wherein scattering parameters S11 and S21 are calculated by the controller/computer from the electrical pulse reflection by applying a Fast Fourier Transform (FFT) algorithm to the electrical pulse reflection, and wherein the complex permittivity curve of the fluid oil and water mixture is calculated by the controller/computer from the scattering parameters S11 and S21, and wherein the controller/computer further correlates the determined time period and the determined resonance points and the calculated complex permittivity curve to the previously determined, and known, complex permittivity curves of the volume fraction of water, and the volume fraction of oil as provided in the database, and as adjusted for temperature to identify the volume fraction of water, and the volume fraction of oil in the fluid thereby allowing the controller/computer to determine an oil/water ratio of the fluid; providing a density probe having an elongate support with a handle end, and an opposing distal end, and wherein the elongate support carries a first pressure transducer which is located proximate to the handle end and which is exposed to the fluid, and a second pressure transducer is located at the distal end, opposite the handle end, and is simultaneously exposed to the fluid, and wherein a known predetermined distance is established between the first pressure transducer, and the second pressure transducer; operationally coupling the controller/computer with the first pressure transducer and the second pressure transducer, and determining a pressure differential between the first pressure transducer and the second pressure transducer so as to calculate the density of the fluid based upon the identified volume fraction of water, and the identified volume fraction of oil as adjusted for temperature as previously provided by the temperature probe; and providing a user interface electronically coupled with the controller/computer, and which receives the measurement of the oil water ratio, and the density of the fluid, and which further generates a user perceivable output which identifies the oil water ratio and the density of the fluid.

A third aspect of the present invention is a probe for measuring multiple parameters of fluid comprising a generally planar metallic body having a first end and an opposing second end, a first edge and an opposing second edge, a first surface and an opposing second surface with a thickness between the first surface and the second surface, and a chrome alumina oxide coating extending entirely about the body; an elongated gap defined by the body generally medially between the first edge and the second edge, the elongated gap communicating with an end of the body; a first ground plate defined by the body between the first edge and a proximate edge of the elongated gap, the first ground plate structurally attached to the body proximate the first end and extending toward the second end; a second ground plate defined by the body between the second edge and a proximate edge of the elongated gap, the second ground plate structurally attached to the body proximate the first end and extending toward the second end; and an elongate center conductor within the elongated gap and extending parallel to and between the first ground plate and the second ground plate, the center conductor having an end portion terminating within the elongated gap between the first ground plate and the second ground plate.

A fourth aspect of the present invention is an apparatus for identifying and measuring volume fraction constituents of a fluid, comprising a source of fluid with a known temperature, and having a volume fraction constituent, and wherein the volume fraction constituent has a previously calculated and known dielectric constant and previously calculated and known resonance points, and wherein information about the previously calculated, and known dielectric constant and resonance points is stored in and is accessible from a database; a probe exposed, at least in part, to the fluid, and wherein the probe has a known length; an electrical pulse emitter which electronically generates an electrical pulse which is delivered to the probe, and which travels the known length of the probe and which generates an electrical pulse reflection; an electrical pulse sampler which electronically communicates with the probe and which further receives and senses the electrical pulse reflection generated by electrical pulse within the probe; a controller/computer electronically coupled with the probe, the electrical pulse emitter, the electrical pulse sampler, and the database, and wherein the controller/computer determines a time period between the electrical pulse emission into the probe and the receipt of the sensed electrical pulse reflection, and wherein the resonance points of the volume fraction constituent is calculated by the controller/computer from the time period which is determined, and wherein the controller/computer further correlates the determined time period to the previously calculated, and known dielectric constant and previously calculated and known resonance points of the volume fraction constituent as provided in the database so as to identify the volume fraction constituent in the fluid and determine a volume of the volume fraction constituent in the fluid; and a user interface electronically coupled with the controller/computer, and which further generates a user perceivable output which identifies the volume fraction constituent of the volume of the volume fraction constituent.

A fifth aspect of the present invention is a method for identifying and measuring a volume fraction constituent of a fluid, the method comprising providing a source of fluid, the fluid having a volume fraction constituent, and wherein the volume fraction constituent has a previously calculated and known dielectric constant, and previously calculated and known resonance points; providing a database having accessible stored information about the previously calculated and known dielectric constant of the volume fraction constituent and having accessible and stored information about the previously calculated and known resonance points of the volume fraction constituent; providing a probe exposed, at least in part, to the fluid, and wherein the probe has a known length; providing an electrical pulse emitter which electronically generates an electrical pulse which is delivered to the probe, and which further travels the known length of the probe and which generates an electrical pulse reflection; providing an electrical pulse sampler electronically coupled with the probe and which further receives and senses the electrical pulse reflection generated by electrical pulse within the probe; providing a controller/computer electronically coupled with the probe, the electrical pulse emitter, the electrical pulse sampler and the database, and wherein the controller/computer determines a time period between the electrical pulse emission into the probe, and the receipt of the sensed electrical pulse reflection, and wherein the resonance points of the volume fraction constituent are calculated by the controller/computer from the determined time period, and wherein the controller/computer further correlates the determined time period to the previously calculated and known dielectric constant and the previously calculated and known resonance points of the volume fraction as provided in the database to identify the volume fraction constituent in the fluid; and providing a user interface electronically coupled with the controller/computer, and which further generates a user perceivable output which identifies the volume fraction constituent in the fluid.

A sixth aspect of the present invention includes applying a Fast Fourier Transform (FFT) to the determined time period to determine the resonance points which may be resonance frequencies of the volume fraction constituent.

A seventh aspect of the present invention includes providing a pipe having a known interior diameter communicating with a source of a volume of the fluid so that the fluid moves through the pipe at a velocity; providing a first probe exposed, at least in part, to the fluid moving through the pipe; providing a second probe exposed at least in part to the fluid moving through the pipe a known distance downstream from the first probe; generating a first output by the first probe when a volume fraction constituent is sensed by the first probe and generating a second output by the second probe when the same volume fraction constituent is subsequently sensed by the second probe, and communicating the first and second probe outputs to the controller/computer; and determining a velocity of each volume fraction constituent moving through the pipe by calculating a time difference between the first probe output and the second probe output and determining the volume of each volume fraction constituent moving through the pipe.

An eighth aspect of the present invention includes maintaining fluid pressure about the probes at a pressure at least equal to the pressure of the source of the fluid to prevent boiling of the fluid within the pipe.

A ninth aspect of the present invention is a method for identifying and measuring a volume fraction constituent of a fluid comprising determining a dielectric constant of a volume fraction constituent by determining a time delay between an electrical pulse emission into a probe exposed, at least in part, to the fluid and a reflection of the electrical pulse from the probe; correlating the determined time delay to a database of known dielectric constants of known volume fraction constituents which generate similar time delays to identify the volume fraction constituent; applying a Fast Fourier Transform (FFT) to the determined time delay to generate a sine wave frequency of the volume fraction constituent; calculating a Power Spectral Density (PSD) calculation to determine the power and resonance points of the sine wave frequency; correlating the determined resonance points of the volume fraction constituent to a database of known resonance points of known concentration of volume fraction constituents to identify the volume fraction constituent; and providing a user interface which generates a user perceivable output of the identified and measured volume fraction constituents in the fluid in a user perceivable form.

A tenth aspect of the present invention includes providing a pipe having a known interior diameter communicating with the source of the fluid so that a volume of the fluid moves through the pipe at a velocity; providing a first probe exposed, at least in part, to the fluid passing through the pipe; providing a second probe exposed at least in part to the fluid moving through the pipe a known distance downstream from the first probe; generating a first output by the first probe when a volume fraction constituent is sensed by the first probe, and generating a second output by the second probe when the same volume fraction constituent is subsequently sensed by the second probe, and communicating the first and second probe outputs to the controller/computer; and determining a velocity of the volume fraction constituent moving through the pipe by calculating a time difference between the first probe output and the second probe output with the known interior diameter of the pipe and known volume of fluid moving through the pipe; and correlating the resonance points of the volume fraction constituent to the resonance points for various concentrations of volume fraction constituents in the fluid the volume of the volume fraction constituent is determined.

An eleventh aspect of the present invention includes a method and apparatus that allows measurement of a parameter proportional to the free water fraction in oil-based drilling fluids.

A twelfth aspect of the present invention includes a method and apparatus that allows the measurement of a parameter proportional to the oil fraction in oil-based drilling fluids.

A thirteenth aspect of the present invention includes a method and apparatus that allows the measurement of a parameter proportional to the free water content in water-based drilling fluid corrected by temperature.

A fourteenth aspect of the present invention includes a method and apparatus using a density probe to determine the local density of drilling fluid that can be measured by first "zeroing-out" the pressure cells and then inserting the probe into the drilling fluid to a specified depth. The density probe will record the temperature, apply the temperature correction for density as a function of temperature based on the water content and oil content per the type of drilling fluid and compute the density.

A fifteenth aspect of the present invention includes a method and apparatus that is capable of correcting a density value that will be used in conjunction with an EFP probe measurement to adjust the fractional content of oil and water.

A sixteenth aspect of the present invention includes a method and apparatus having two buttons on the handle of the density probe to allow pressure cell measurements to be "zeroed-out" and thereafter allow a pressure reading to be made and the temperature to be determined. The readings collected by the density probe are electrically communicated to a signal processor in the electronics enclosure to compute and record the results.

A seventeenth aspect of the present invention includes a method for measuring multiple parameters of fluid, and wherein the fluid is drilling fluid.

An eighteenth aspect of the present invention includes a method for measuring multiple parameters of fluid, and wherein the EFP probe is portable.

A nineteenth aspect of the present invention includes a method for measuring multiple parameters of fluid, and wherein the density probe is portable.

A twentieth aspect of the present invention includes a method for measuring multiple parameters of fluid, and wherein the EFP probe is substantially permanently interconnected to a pipe communicating with the source of fluid so that the EFP probe is at least partially exposed to the fluid in the pipe.

A twenty-first aspect of the present invention includes a method for measuring multiple parameters of fluid, and wherein the fluid is contained in a reservoir/tank while being measured.

A twenty-second aspect of the present invention is a method for measuring multiple parameters of fluid comprising: providing a source of fluid providing a fluid having a volume fraction of water and a volume fraction of oil, and wherein the volume fraction of water and the volume fraction of oil each have a previously determined and known dielectric constant, previously determined and know resonance points and a complex permittivity curve; providing a database having stored accessible information about the previously determined and known dielectric constants, previously determined and known resonance points of various concentrations and complex permittivity curves of the volume fractions of water and of oil; providing a temperature probe exposed to the fluid to determine the temperature of the fluid; providing an Electric Field Perturbation (EFP) probe exposed to the fluid, and wherein the EFP probe has a known length; providing an electrical pulse emitter that electronically generates an electrical pulse and which is delivered to the EFP probe, and wherein the electrical pulse travels the length of the EFP probe, and subsequently generates an electrical pulse reflection when encountering a change in impedance; providing an electrical pulse sampler electronically coupled with the EFP probe, and which further receives, and senses, the electrical pulse reflection, and which further receives, and senses, the electrical pulse transmitted through the EFP probe; providing a controller/computer electronically coupled with the temperature probe, the EFP probe, the electrical pulse emitter, the electrical pulse sampler, a density probe and the database, and wherein the controller/computer determines a time period between the electrical pulse emission into the EFP probe, and the receipt of the sensed electrical pulse reflection from the EFP probe, and wherein resonance points of the fluid are calculated by the controller/computer from the electrical pulse reflection and transmission by applying a Fast Fourier Transform (FFT) algorithm to the electrical pulse reflection and transmission, and wherein scattering parameters S11 and S21 are calculated by the controller/computer from the electrical pulse reflection and transmission by applying a Fast Fourier Transform (FFT) algorithm to the electrical pulse reflection and transmission, and wherein the complex permittivity curve of the fluid mixture is calculated by the controller/computer from the scattering parameters S11 and S21, and wherein the controller/computer further correlates the determined time period and the determined resonance points and the calculated complex permittivity curve to the previously determined, and known, complex permittivity curves of the volume fraction of water, and the volume fraction of oil as provided in the database, and as adjusted for temperature to identify the volume fraction of water, and the volume fraction of oil in the fluid thereby allowing the controller/computer to determine an oil/water ratio of the fluid; providing a density probe having an elongate support with a handle end, and an opposing distal end, and wherein the elongate support carries a first pressure transducer which is located proximate to the handle end and which is immersed in the fluid, and a second pressure transducer is located at the distal end opposite the handle and is simultaneously immersed in the fluid, and wherein a known predetermined distance is established between the first pressure transducer, and the second pressure transducer; operationally coupling the controller/computer with the first pressure transducer and with the second pressure transducer, and determining a pressure differential between the first pressure transducer and the second pressure transducer so as to calculate the density of the fluid based upon the identified volume fraction of water, and the identified volume fraction of oil as adjusted for temperature as previously provided by the temperature probe; and providing a user interface visual display electronically coupled with the controller/computer, and which receives the determined measurement of the oil-water ratio, and the density of the fluid, and which further generates a user perceivable output which identifies the oil-water ratio and the density of the fluid.

A twenty third aspect of the present invention is a method for measuring multiple parameters of fluid and wherein the EFP Probe has a generally planar metallic body having a first end and an opposing second end, a first edge and an opposing second edge, a first surface and an opposing second surface with a thickness between the first surface and the second surface, and a chrome alumina oxide coating extending entirely about the body; an elongated gap defined by the body generally medially between the first edge and the second edge, the elongated gap communicating with an end of the body; a first ground plate defined by the body between the first edge and a proximate edge of the elongated gap, the first ground plate structurally attached to the body proximate the first end and extending toward the second end; a second ground plate defined by the body between the second edge and a proximate edge of the elongated gap, the second ground plate structurally attached to the body proximate the first end and extending toward the second end; and an elongate center conductor within the elongated gap and extending parallel to and between the first ground plate and the second ground plate, the center conductor having an end portion terminating within the elongated gap between the first ground plate and the second ground plate.

A twenty fourth aspect of the present invention is a method for measuring multiple parameters of fluid and wherein the fluid is drilling fluid.

A twenty fifth aspect of the present invention is a method for measuring multiple parameters of fluid and wherein the EFP probe is portable.

A twenty sixth aspect of the present invention is a method for measuring multiple parameters of fluid and wherein the density probe is portable.

A twenty seventh aspect of the present invention is a method for measuring multiple parameters of fluid and wherein the EFP probe is substantially permanently interconnected to a pipe communicating with the source of fluid so that the EFP probe is at least partially exposed to the fluid in the pipe.

A twenty eighth aspect of the present invention is a method for measuring multiple parameters of fluid and wherein the fluid that is being measured is contained in a reservoir/tank A twenty ninth aspect of the present invention is a method for measuring multiple parameters of fluid comprising: providing a source of fluid that provides a fluid having volume fractions, and wherein the volume fractions each have a previously determined and known dielectric constant, previously determined and know resonance points and a previously determined and known complex permittivity curve; providing a database having stored accessible information about the previously determined and known dielectric constants, previously determined and known resonance points of various concentrations of the volume fractions and previously determined and known complex permittivity curves of the volume fractions; providing a temperature probe exposed to the fluid to determine the temperature of the fluid; providing a density probe having a first pressure transducer and a second pressure transducer that are spaced apart by a known distance and which are simultaneously immersed in the fluid; providing an Electric Field Perturbation (EFP) probe immersed in the fluid, and wherein the EFP probe has a known length; providing an electrical pulse emitter that electronically generates an electrical pulse and which is delivered to the EFP probe, and wherein the electrical pulse travels along the length of the EFP probe, and subsequently generates an electrical pulse reflection when the electrical pulse encounters a change in impedance; providing an electrical pulse sampler electronically coupled with the EFP probe, and which further receives, and senses, the electrical pulse reflection; providing a controller/computer electronically coupled with the temperature probe, the EFP probe, the electrical pulse emitter, the electrical pulse sampler, the density probe and the database; performing, with the controller/computer, a time domain evaluation of the fluid and correlating the time domain evaluation results to the previously determined and known dielectric constants and resonance points and complex permittivity curves stored in the database to identify the volume fraction constituents of the fluid; performing, with the controller/computer, a frequency domain evaluation of the time domain evaluation results by performing a Fast Fourier Transform of the time domain evaluation results to generate a sine wave and further perform a Power Spectral Density calculation of the sine wave to determine a frequency and amplitude of the sine wave to identify resonance points of the fluid, and correlating the identified resonance points of the fluid to the previously determined and known resonance points of volume fractions stored in the database; and providing a user interface electronically coupled with the controller/computer, and which further generates a user perceivable output which identifies the oil-water ratio and the density of the fluid.

BRIEF DESCRIPTIONS OF THE DRAWINGS

FIG. 5 is an orthographic side view of the pressure density probe showing two spaced apart density probe transducers carried on an elongate support having an operator handle opposite the density probe transducers.

FIG. 6 is an enlarged view of two pressure density transducers of FIG. 5

Figure 16:
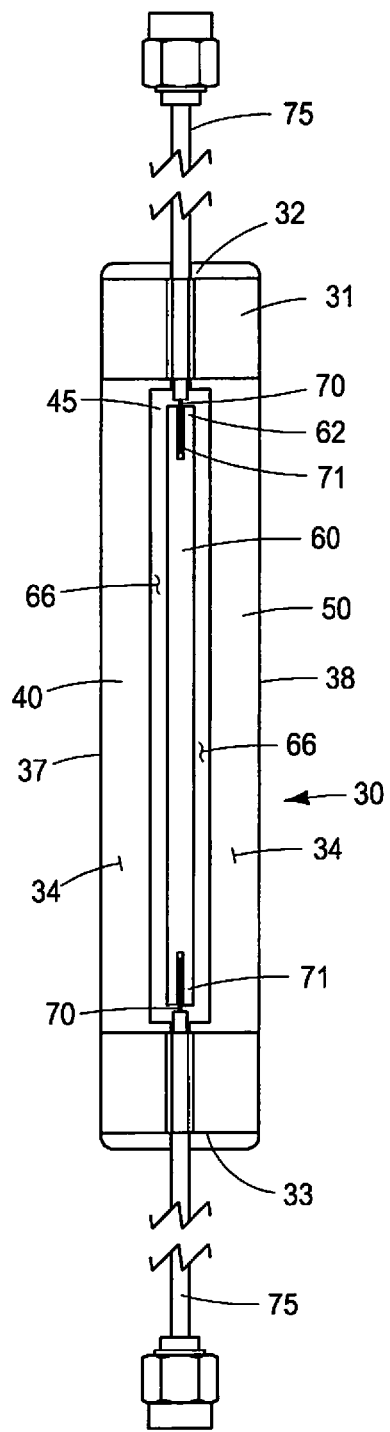
FIG. 16 is an orthographic front view of a second configuration of an EFP probe configured for an extension tail to delay signal reflection.
Figure 17:
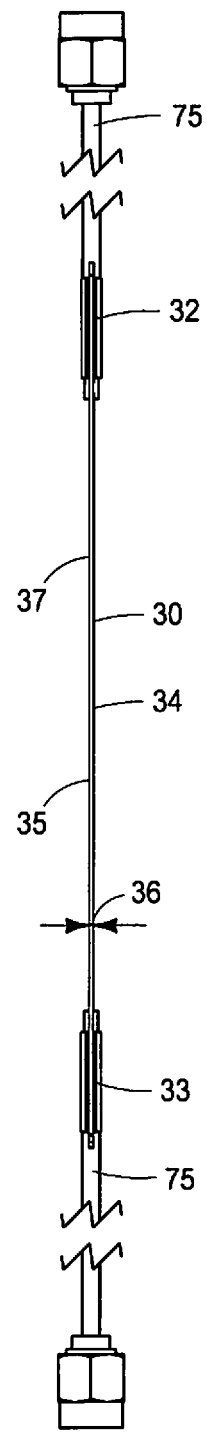

FIG. 17 an orthographic side view of the EFP probe of FIG. 16.

Figure 18:
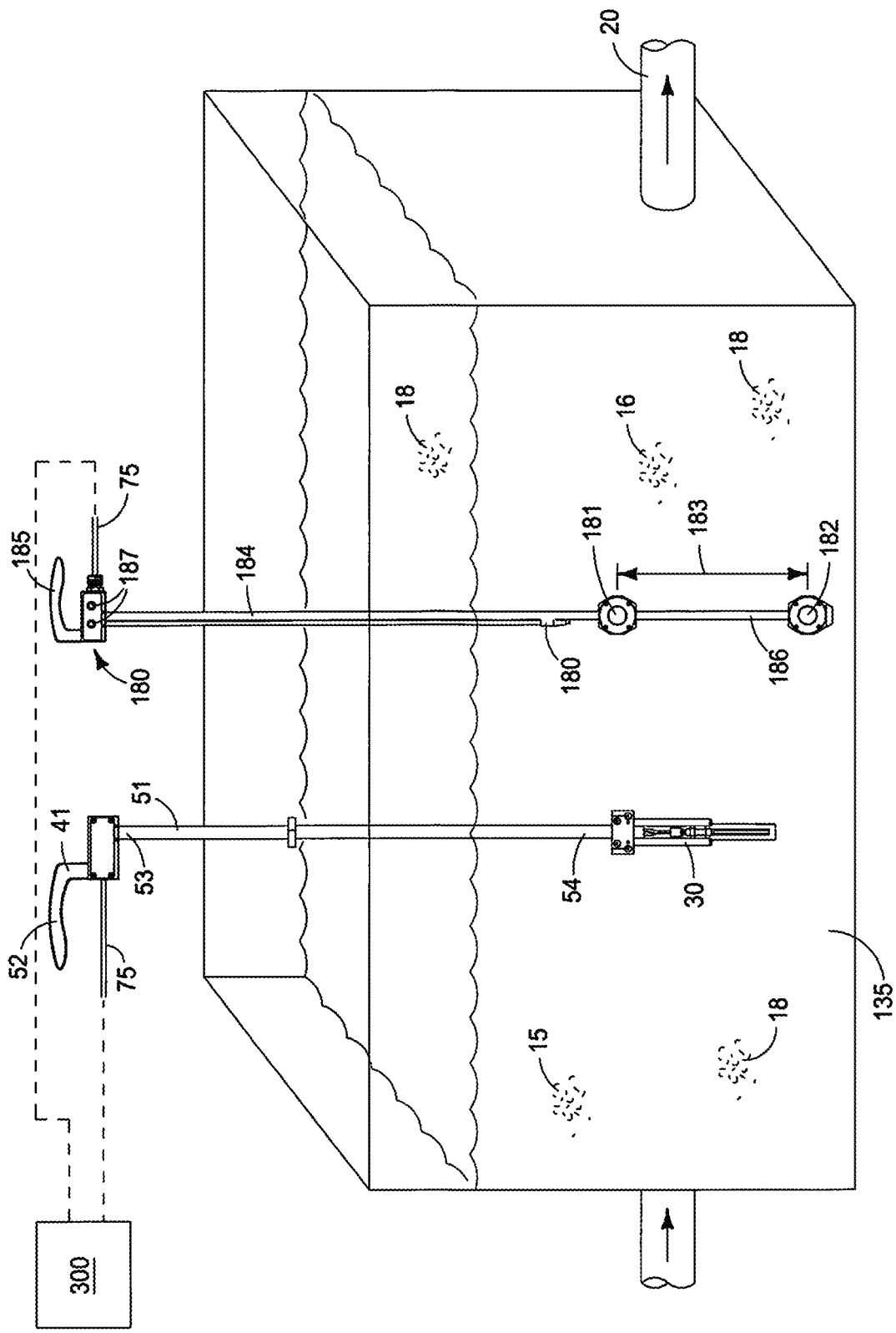

FIG. 18 is a cutaway view of a discharge/settling tank containing drilling fluid and volume fractions and showing the portable EFP probe and the density probe immersed in the fluid to take the measurements.

Figure 19:
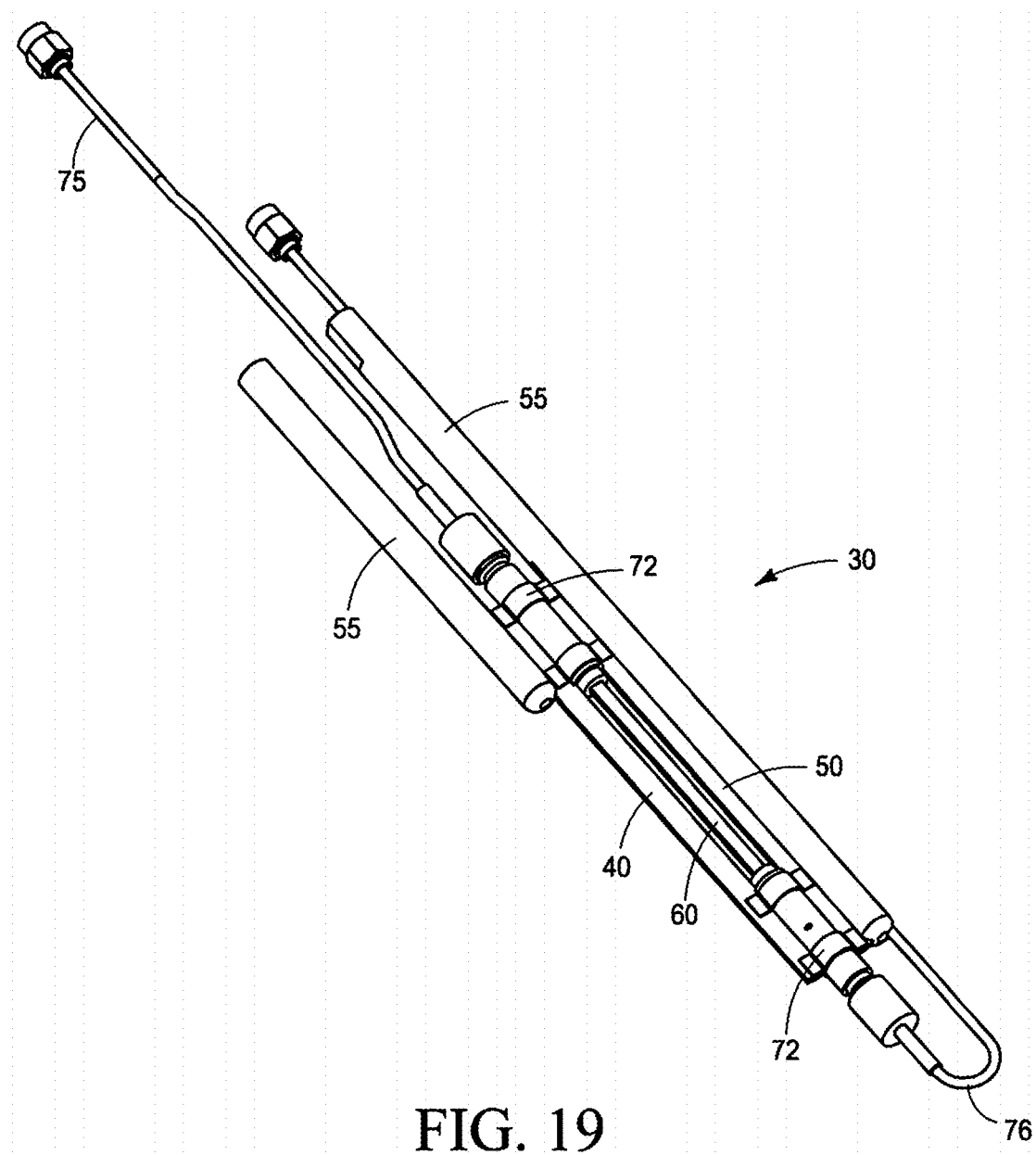

FIG. 19 is an isometric front, side and end view of a configuration of an EFP probe that may be used as an extension tail probe or as a through signal probe.

Figure 20:
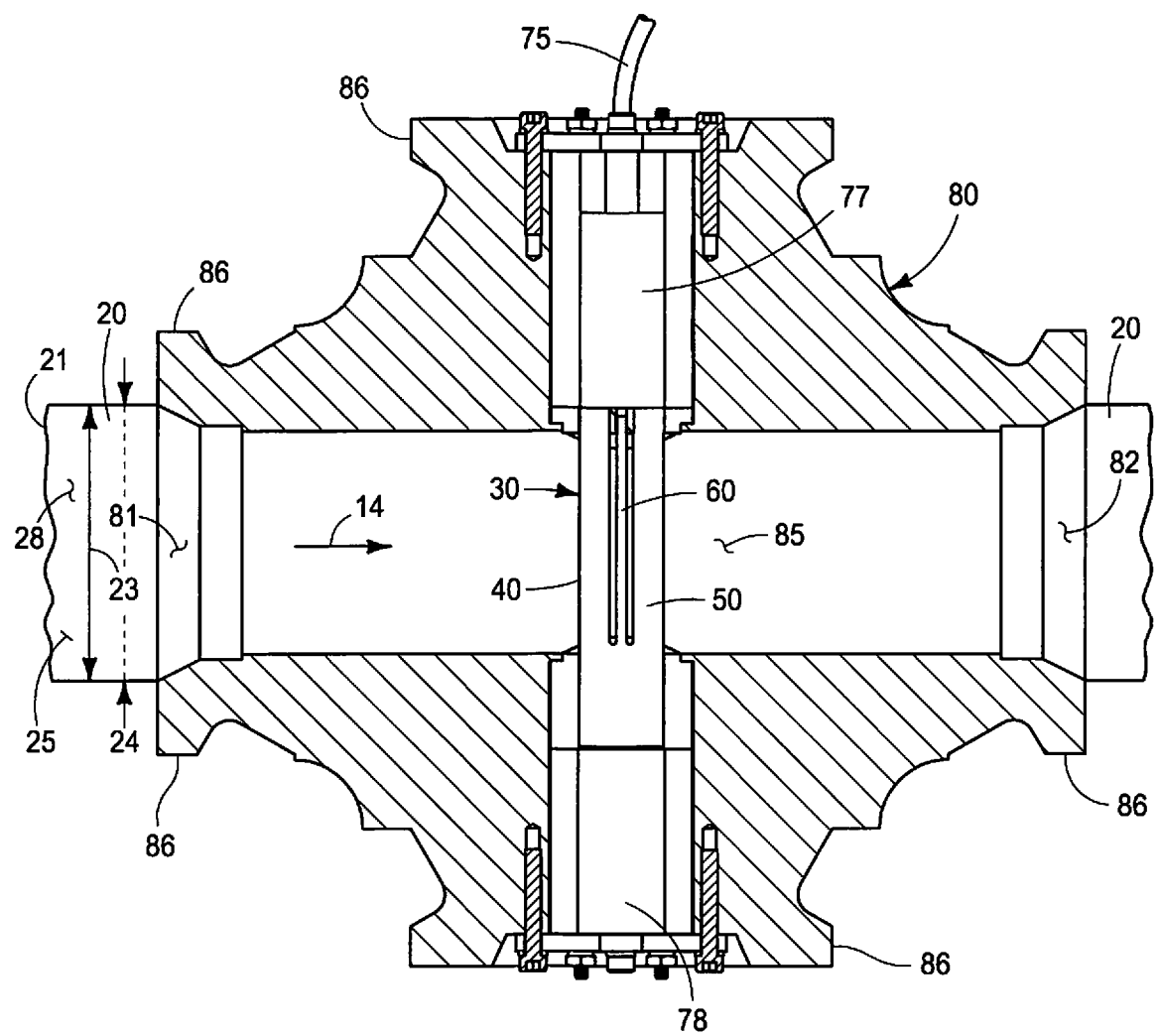

FIG. 20 is an orthographic cross section view of an EFP probe carried within a grayloc support such as may be used in a fixed installation of the instant system.

Figure 21:
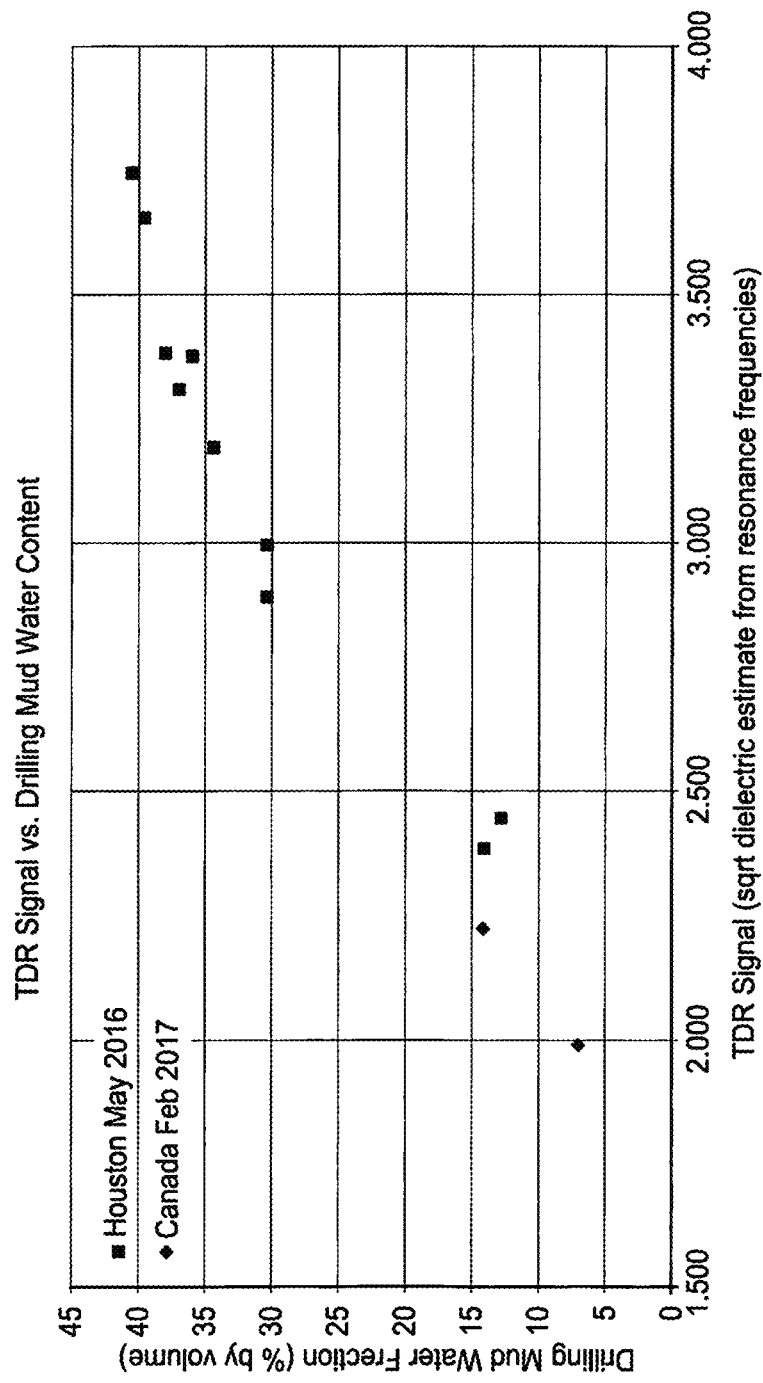

FIG. 21 is a graph showing a plot of the TDR signal (EFP signal) relative to measured water content.

Figure 22:
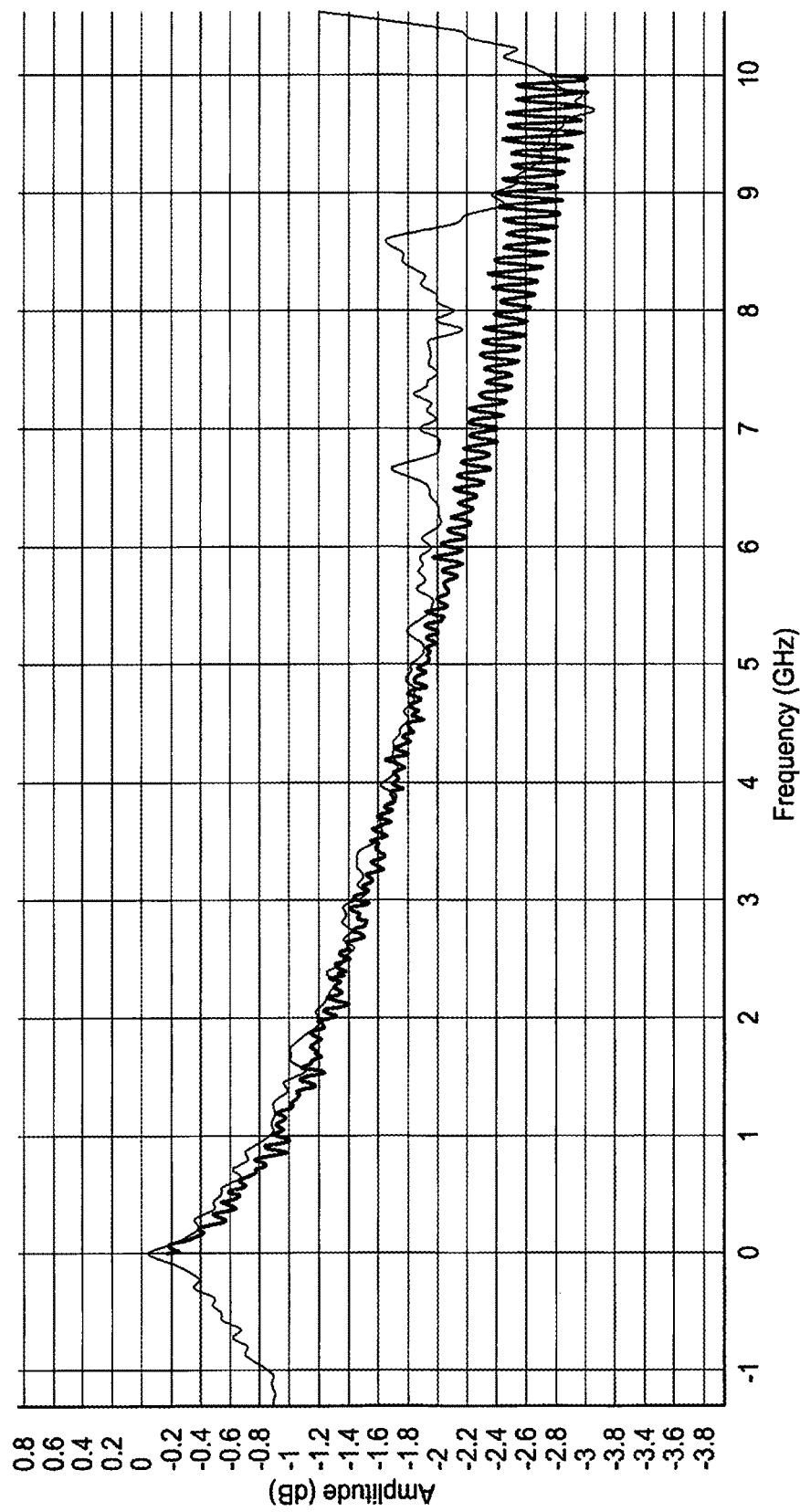

FIG. 22 is a graph for measurement of two S11 scattering parameters taken with two different instruments.

Figure 23:
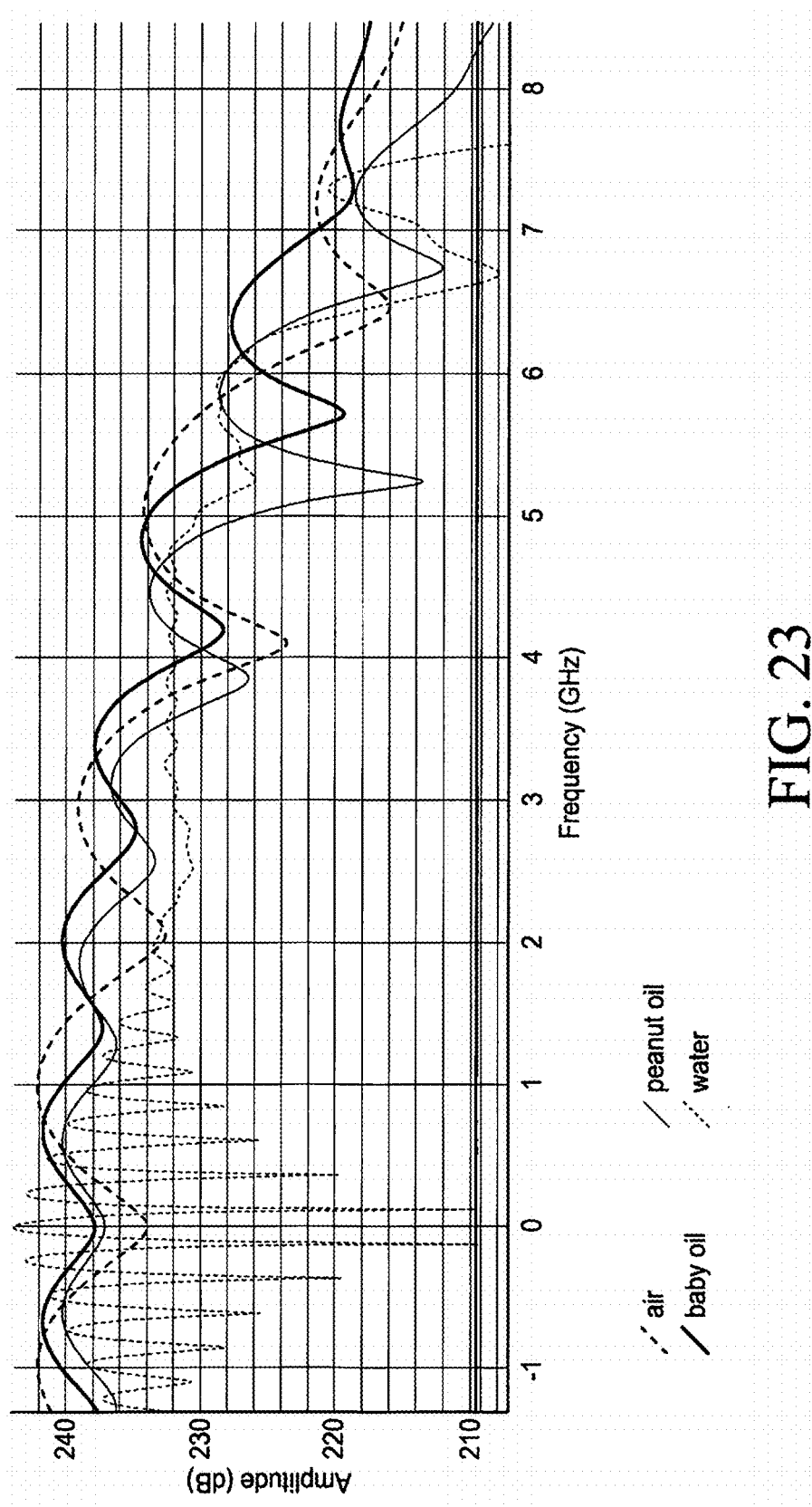

FIG. 23 is a graph of resonance points of the EFP probe in water, in baby oil, in peanut oil, and in air.

Figure 24:
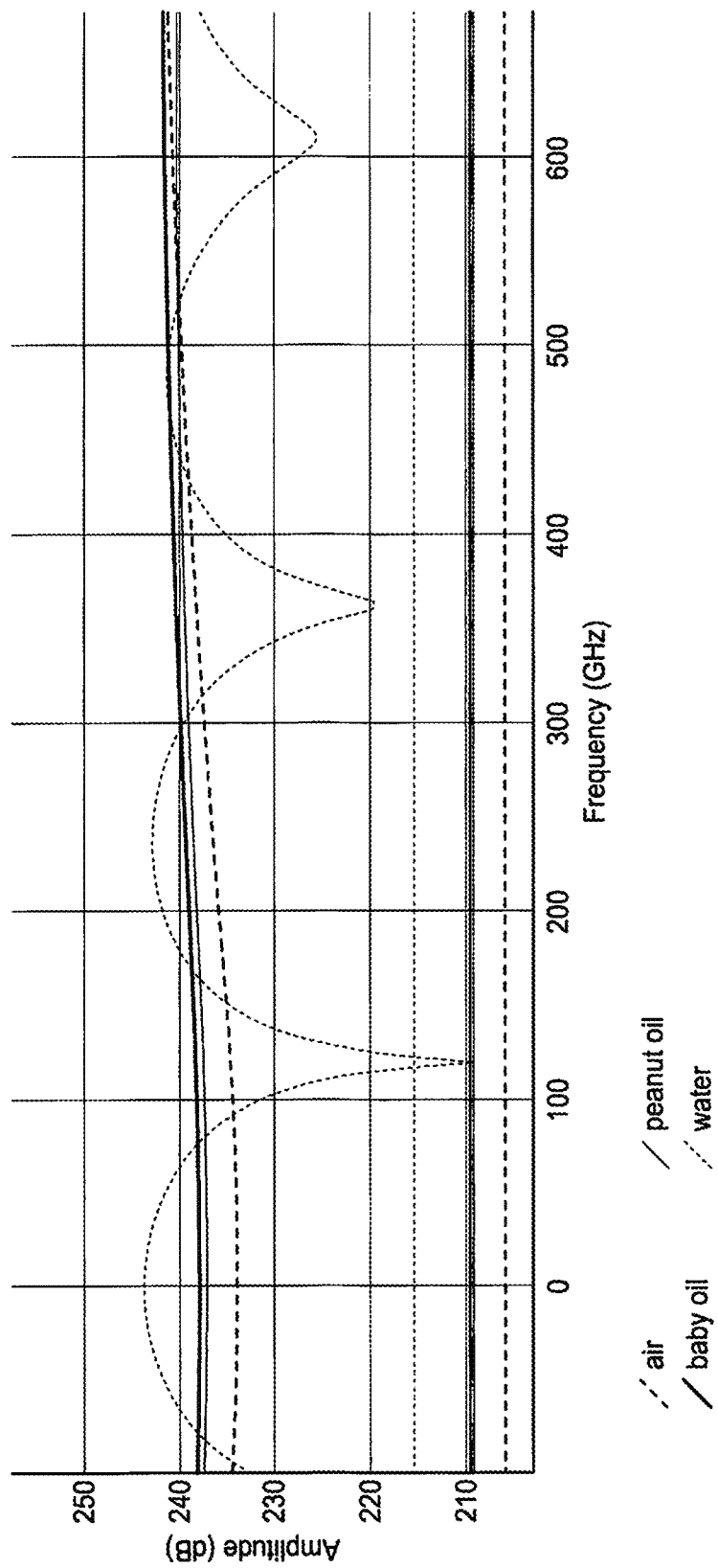

FIG. 24 is a graph of a frequency domain representation of an EFP probe reflection while the probe is immersed in water, showing the resonance points.

Figure 25:
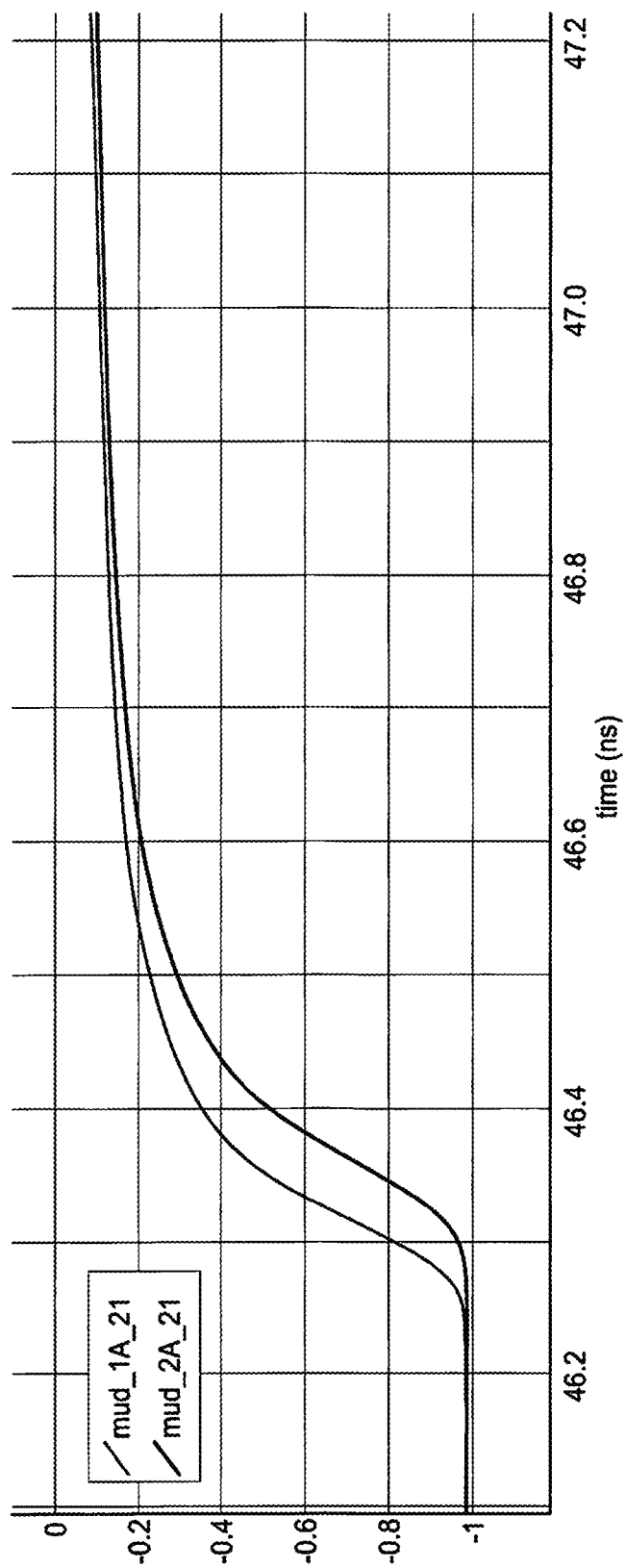

FIG. 25 is a graph of the dielectric constant of two similar oil based drilling fluids, showing the "mud_2A_21 graph" representing a drilling fluid that has a higher percentage of water than the "mud_1A_21 graph".

Figure 26:
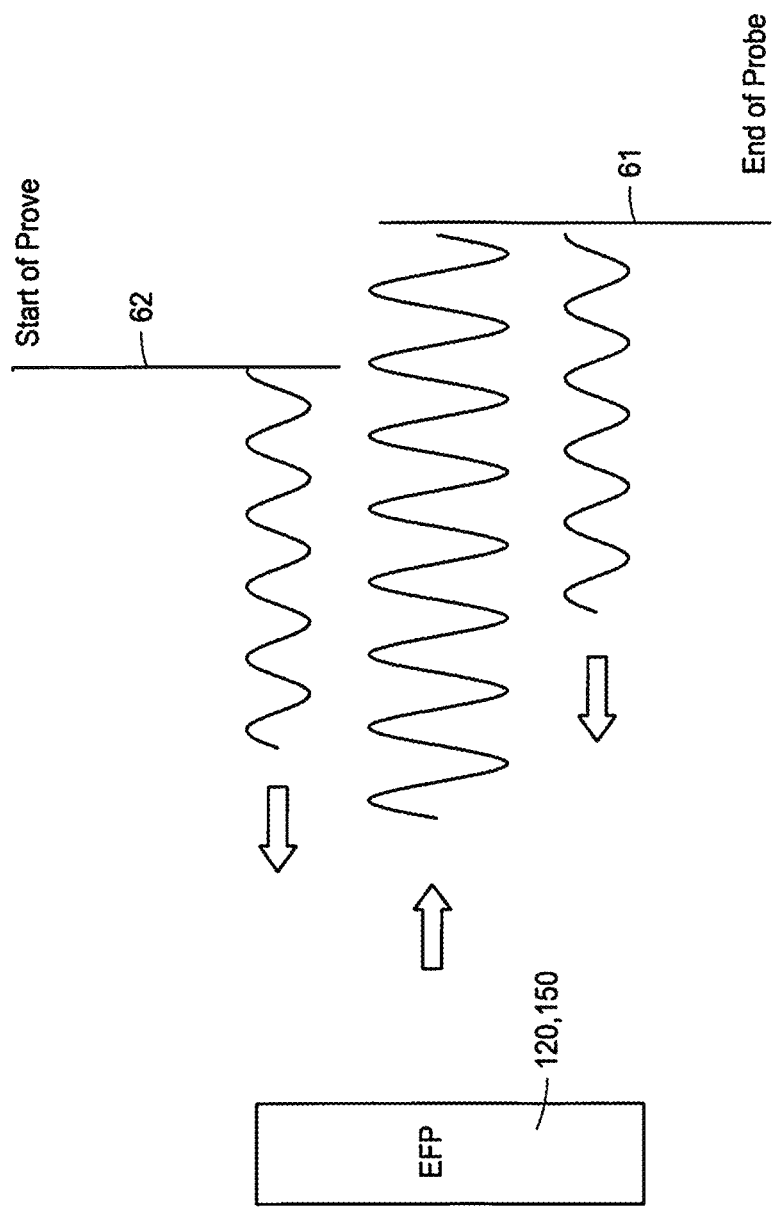

FIG. 26 shows sine waves reflecting from the start of the EFP probe, for the end of the EFP Probe and the destructive interference.

Figure 27:
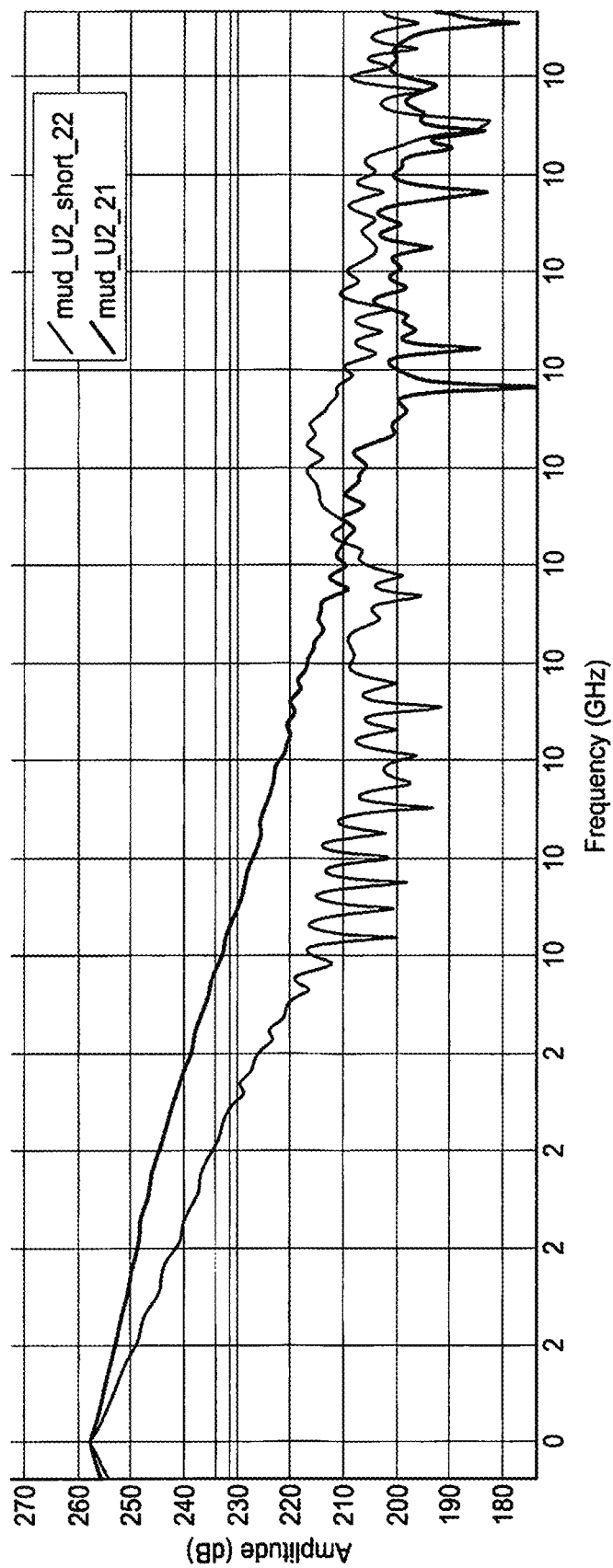

FIG. 27 is a graph showing the resonance points of air, baby oil, peanut oil and water.

DETAILED DESCRIPTION OF THE PREFERRED EMBODIMENTS

This disclosure of the invention is submitted in furtherance of the Constitutional purposes of the U.S. Patent Laws "to promote the progress of science and useful arts" (Article 1, Section 8).

A method and apparatus for measuring multiple parameters of fluid generally comprises a source of fluid 13, an Electric Field Perturbation (EFP) probe 30, a density probe 180, a pulse emitter 120, a pulse sampler 150, a controller 170 which may be a computer, and an operator visual display 200.

The source of fluid 13 is typically an oil well, or grouping of oil wells producing a fluid 14 that contains a mixture of various volume fractions including, but not limited to, oil 15, water 16 and drilling fluid 17. The source of fluid 13 may also be a stream of fluid 14 or a volume of fluid 14 in a tank/reservoir 135 used in the drilling of a well 138 and including without limitation, drilling fluid or "drilling mud". It is also contemplated the source of fluid 13 may be a volume of stored fluid 14 such as a volume of fuel (not shown) or oil 15 within a storage tank 135. When produced from the source of fluid 13, the fluid 14 may be at pressure and is typically at a temperature that may exceed ambient temperature by hundreds of degrees, although the temperature and pressure vary over time and conditions. It is further contemplated and anticipated the fluid 14 volume fraction constituents 15, 16, 17 may be produced, and flow through a pipe 20, in segregated fashion, and at other times it is anticipated the volume fraction constituents 15, 16, 17 may be a mixture or emulsions of fluid 14 that may, or may not be, homogeneously distributed within the pipe 20 or reservoir.

Oil 15, water 16 and drilling fluid 17 are different molecular compounds, and have different, well recognized dielectric constants and resonance points depending upon concentration. The dielectric constant of water 16 ranges from approximately 80 for cold water down to approximately 25 for very hot water. The dielectric constant of steam is approximately 1.01 increasing to approximately 1.15 as temperature increases. The dielectric constant of oil 15 is approximately 2.0 to 2.5 depending upon the density of the oil 15. The dielectric constant of drilling fluid 17 varies widely depending upon its constituents.

Figure 13:
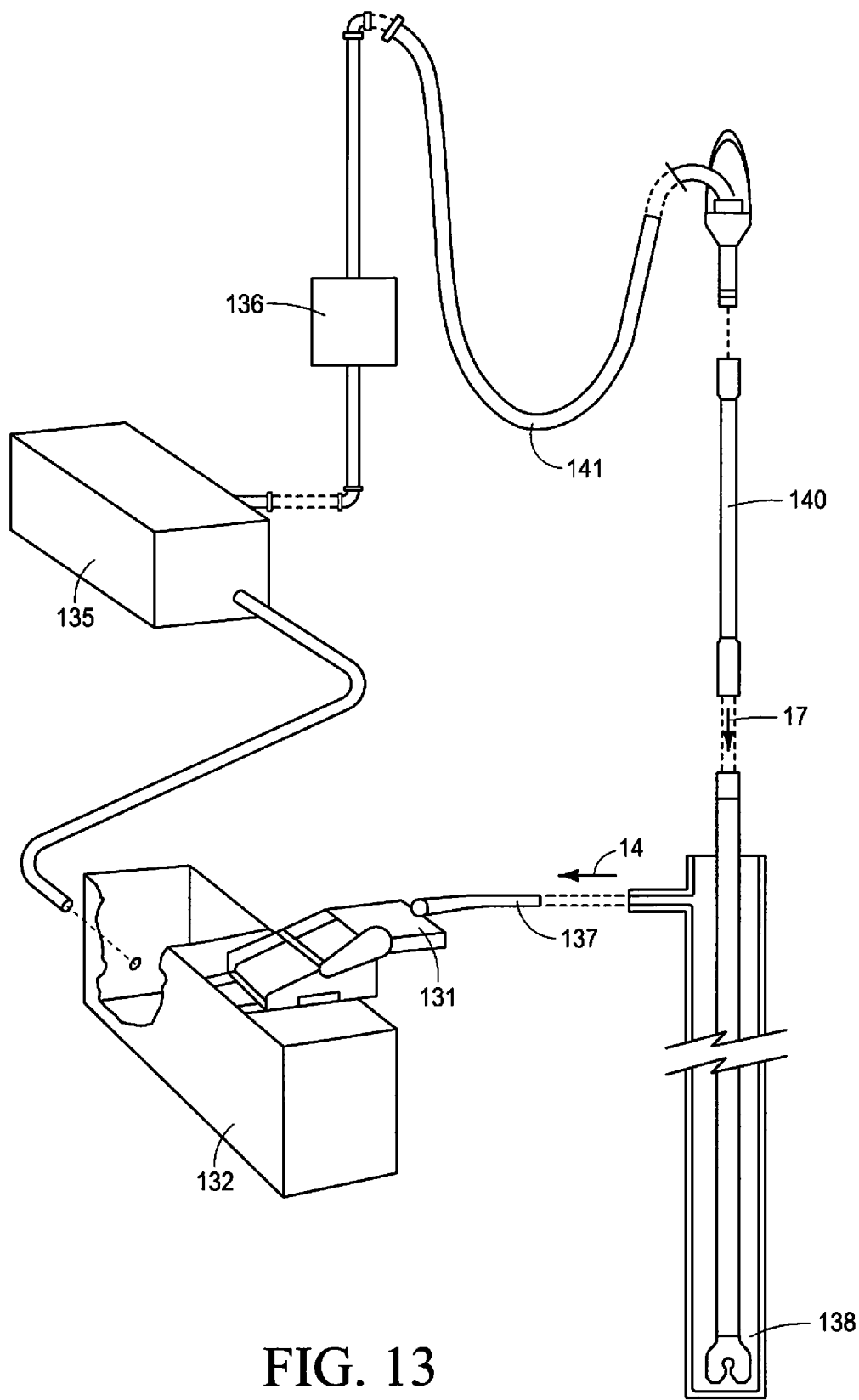
FIG. 13 is a simplified block diagram of the components of a petroleum well drilling rig showing the relationship of the various components.

The pipe 20 has an inflow end 21 communicating with the source of fluid 13 and an outflow end 22 communicating with a distribution point (not shown) such as a collection facility (not shown). The pipe 20 has a known interior diameter 23, an exterior diameter 24, an exterior surface 25, defines a medial channel 28 and may contain a plurality of connections 26 where fittings 27 and apparatus and the like may be joined to the pipe 20, and also where the pipe 20 may connect to other sections of pipe 20 to extend the length thereof. When the invention is used in the drilling of a well to identify and measure components produced in a well drilling operation, the pipe 20 may communicate with drilling apparatus such as, but not limited to, a shaker 131, a discharge tank 132, a centrifuge separator 133, a reserve tank 134, a mixing/suction tank 135, a flow meter 90, a high pressure mud pump 136 and related structures/apparatus which serves as the source of fluid 13. (See FIGS. 1 and 13) Further the pipe 20 may communicate with other pipes 20 that carry drilling fluids 17 and the like to and from a well bore 138, some of which may be under high pressure, such as downstream of a high pressure pump 136 and some of which may be before or after the separation of particulated solids from the fluid 14, such as by a shaker 131 or a centrifuge 133.

A temperature sensor 100 and a flow meter 90 may be interconnected with the pipe 20 downstream of the source of fluid 13. The temperature sensor 100 and flow meter 90 are known apparatus and communicate with the medial channel 28 of the pipe 20 to monitor and sense the temperature of and movement of fluid 14 through the pipe 20. Information and data sensed by the temperature sensor 100 and the flow meter 90 are communicated to the controller/computer 170.

Figure 7:
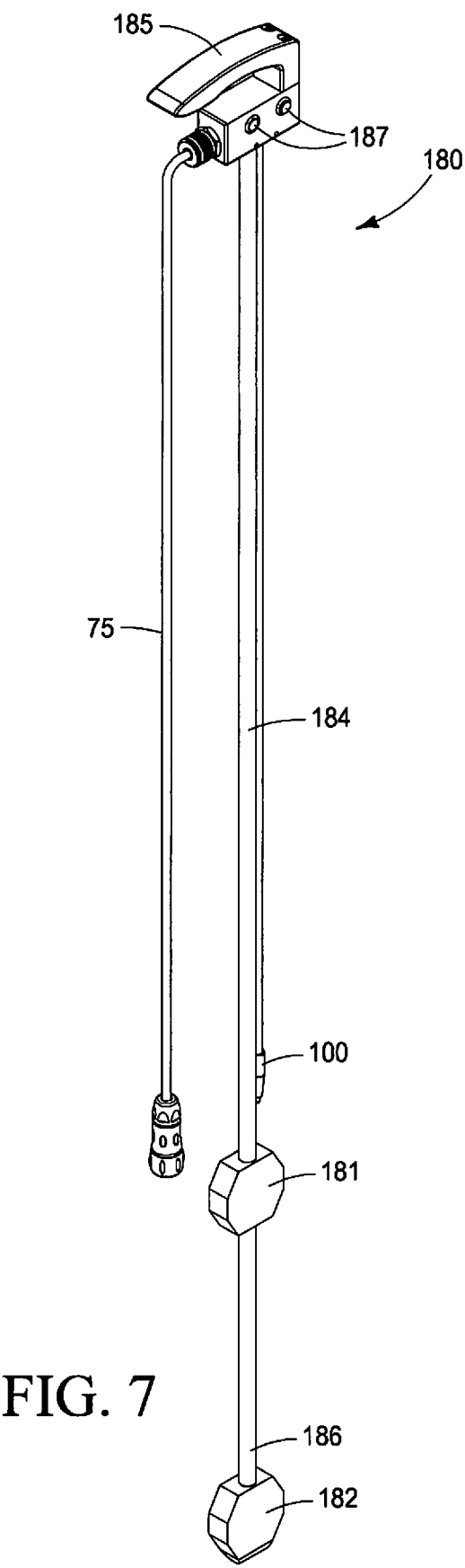
FIG. 7 is an isometric front, side and top view of the pressure density probe of FIG. 5.
Figure 8:
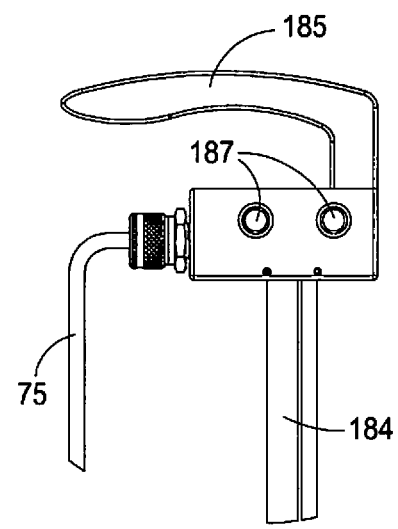
FIG. 8 is an enlarged orthographic side view of the pressure density probe handle showing the operator control buttons.
Figure 14:
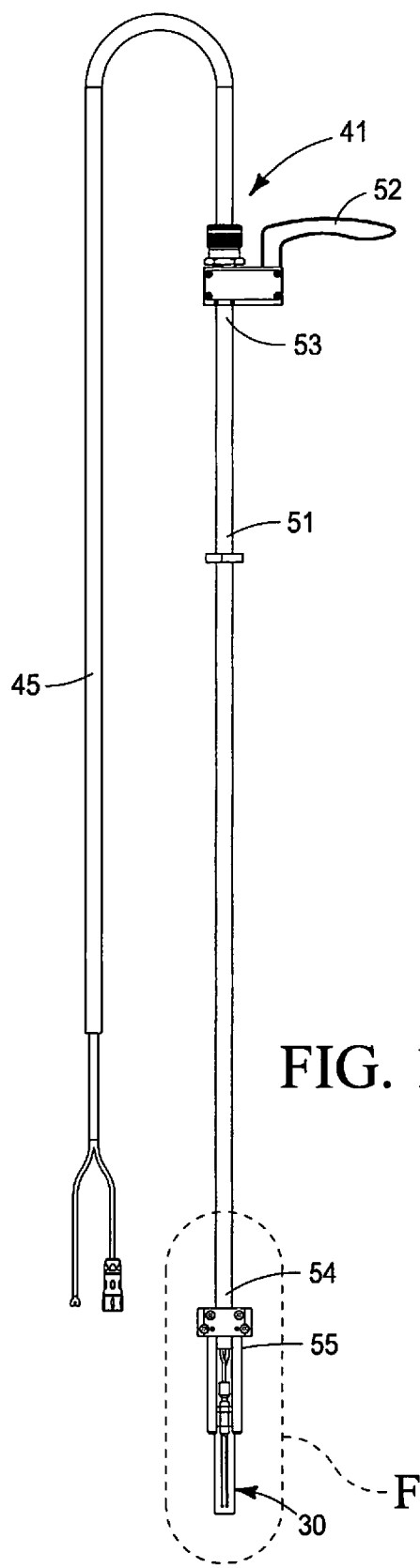
FIG. 14 is an orthographic front view of the portable EFP probe, handle and electrical cable.

As shown in FIGS. 7 and 14 representing a configuration of the instant method and apparatus that is portable 41, the EFP probe 30 is positionally supported at an end of an elongated support 51 having a handle 52 at a first end 53 and an opposing distal end 54 opposite the handle 52. A probe support assembly 55 is carried at the distal end 54 of the elongated support 51 and the probe support assembly 55 carries the EFP probe 30 in a manner so that the EFP probe 30 is electrically isolated from the elongated support 51. A coaxial cable 75 operatively communicates with the EFP probe 30. Operator controls (not shown) on the handle 52 to allow an operator to control operation of the portable EFP probe 41 and length of the elongated support 51 between the handle 52 and the EFP Probe 30 at the distal and 54 allow an operator to fully submerge the EFP probe 30 within the fluid 14 being tested/measured. (See FIG. 18).

As shown in FIG. 16, the EFP probe 30 has a body 31 that is generally planar and rectilinear. The body 31 has a first end 32 and an opposing second end 33, a first surface 34, and an opposing second surface 35 with a thickness 36 of approximately 0.050 inches between the first surface 34 and the second surface 35. The body 31 further has a first edge 37, and an opposing second edge 38 and defines a dimensionally enlarged support shoulder (not shown) in the first edge 37 and the second edge 38 spaced apart from the first end 32. The body 31 further defines an elongated medial slot 45 between a first ground plate 40 at the first edge 37 and a second ground plate 50 at the second edge 38. An elongated center conductor 60 is carried within the medial slot 45 and has a root end 61 that may be structurally attached to the probe body 31 proximate the second end 33 between the first and second ground plates 40, 50 respectively, and the center conductor 60 has a free terminal end 62 within the medial slot 45 proximate to the body 31 first end 32. The free terminal end 62 of the center conductor 60 carries a conductor adaptor link 70 and a conductor weld pad 71 for electronic connection to a coaxial cable 75. The length of the center conductor 60 defines the active length of the probe 30. The first end 32 of the probe body 31 is known as the "active end" of the probe 30.

As shown in FIG. 16, elongated gap 66 is defined between each laterally outer edge of the center conductor 60 and a proximate edge of the first ground plate 40 and a proximate edge of the second ground plate 50. The gap 66 is engineered to provide optimum sensitivity to the detection of charges in volume fraction constituents 15, 16, 17 by impedance measurements. The gap 66 is uniform along its length and is typically approximately 0.080 inches in width for oil 15, water 16 and mixtures. It is expressly contemplated however, other gap 66 widths may be used and/or engineered to measure the impedances of other volume fraction constituents 15, 16, 17 to be identified and measured in the fluid 14.

The probe body 31 is preferably formed entirely of Inconel® alloy 725 which is highly resistant to the corrosive environment to which the probe body 31 may be exposed during operation. Further, a desirable and durable dielectric oxide coating (not shown) is formed on the probe of body 31 extending entirely thereabout. Inconel® alloy 718 may also be used, but Inconel® alloy 725 is preferred. Inconel® alloy 725 and Inconel® alloy 718 are available from Megamex Specialty Metals of Humble, Tex.

The method of forming the probe 30, which carries the durable dielectric oxide coating on its outer surfaces 34, 35, includes the steps of cutting the desired probe 30 shape from the desired metallic alloy and then oxidizing cleaning the probe body 31 at approximately 1,750° to 2,000° Fahrenheit in air for one to three hours in order to form the highly electrically resistive oxide surface covering the entire body 31 of the probe 30. The temperatures used in formation of the oxide coating reduce cracking of the oxide coating and prevents embrittlement caused by grain growth. Following the one to three-hour heat treatment, the probe body 31 is cooled to less than 1,000° Fahrenheit. Subsequently, the probe body 31 is heated in air to 1,325° Fahrenheit for a period of 8 hours. Thereafter, the probe body 31 is air cooled in an oven to ambient temperature. The heat treatment process forms a chrome alumina oxide coating covering the entire probe body 31 to insulate the probe body 31 in the fluid 14. The oxide coating is preferably approximately 0.5 mm to approximately 3 mm thick and is believed to have a chemical composition of approximately CrMoNbTiAl.

It is desirable that the probe body 31, carrying the chrome alumina oxide coating has an impedance of approximately 90 ohms in air, which allows use of a 90-ohm coaxial cable 75 for interconnection with the pulse emitter 120 and the pulse sampler 150. The use of a 90-ohm coaxial cable 75 allows the probe 30 to measure 100% water 16; water 16 containing very little oil 15; 100% oil 15; and oil 15 containing very little water 16. Providing for such a wide range of measurements of water/oil mixtures allows the probe 30 to measure a full range of "water cuts". Further, the ability to operate at 90 ohms allows the probe 30 to identify drilling fluids 17 and components thereof and also identify and measure effective water 16 content within drilling fluids 17. The ability of the probe 30 to measure water content allows the probe 30 to be used in stationary operations, such as to measure the water 16 content of a standing pool of fluid 14, such as fuel in a fuel tank (not shown), or fluid reservoir 135 that may be contaminated with an unknown amount of water 16. The probe's 30 ability to detect and measure drilling fluids/drilling muds 17 allows the instant invention to be used in the drilling of hydrocarbon producing wells, as well as the use in hydrocarbon producing wells that are in production.

Figure 9:
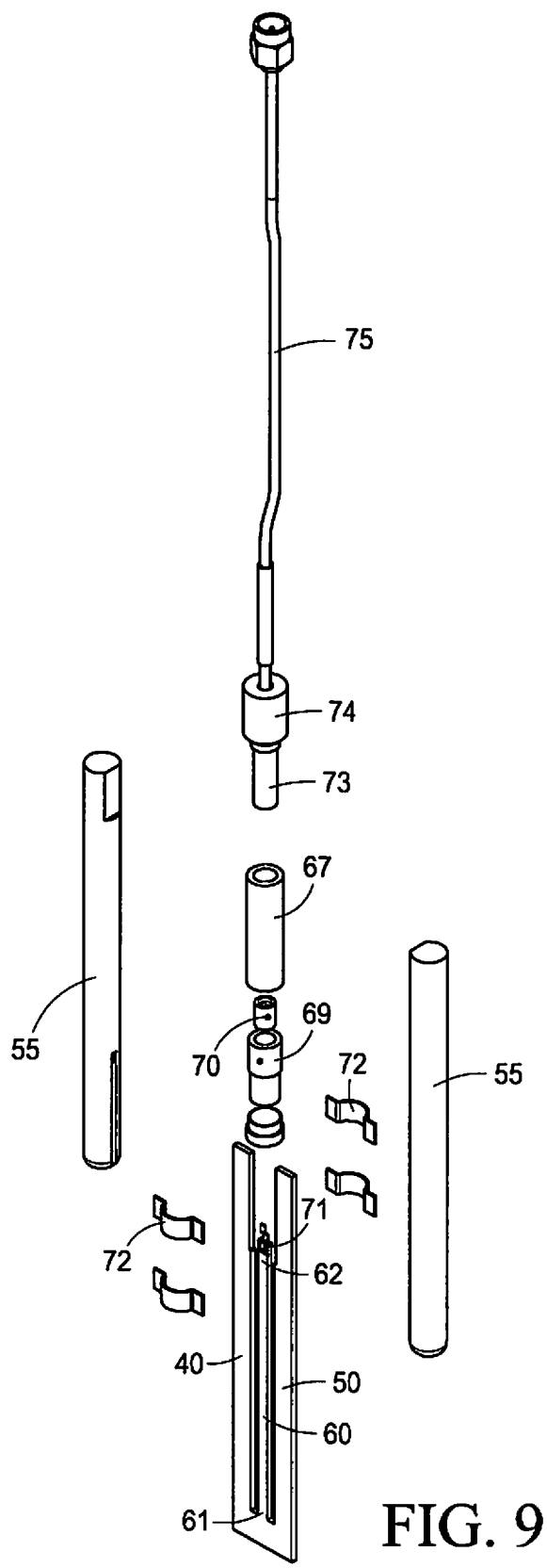
FIG. 9 is an exploded isometric view of a first configuration of EFP probe.
Figure 10:
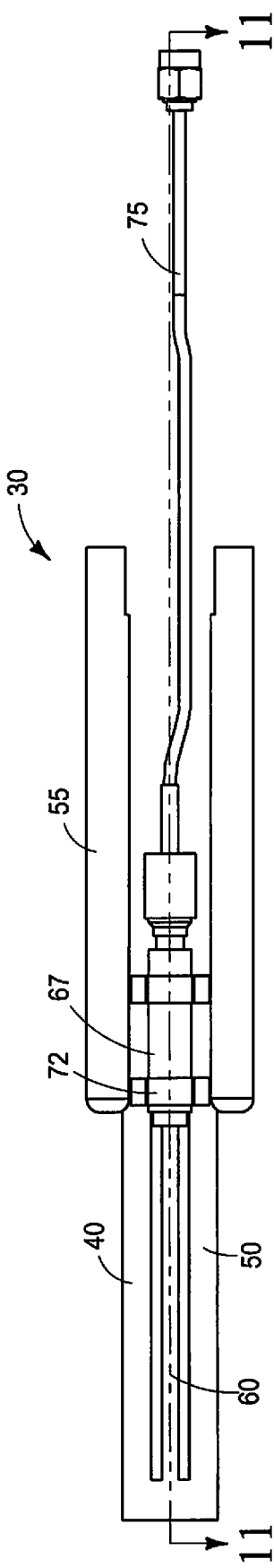
FIG. 10 is an enlarged orthographic side view of the first configuration of EFP probe of FIG. 9.
Figure 11:
FIG. 11 is an orthographic cross section view of the EFP probe taken on line 11-11 of FIG. 10.
Figure 12:
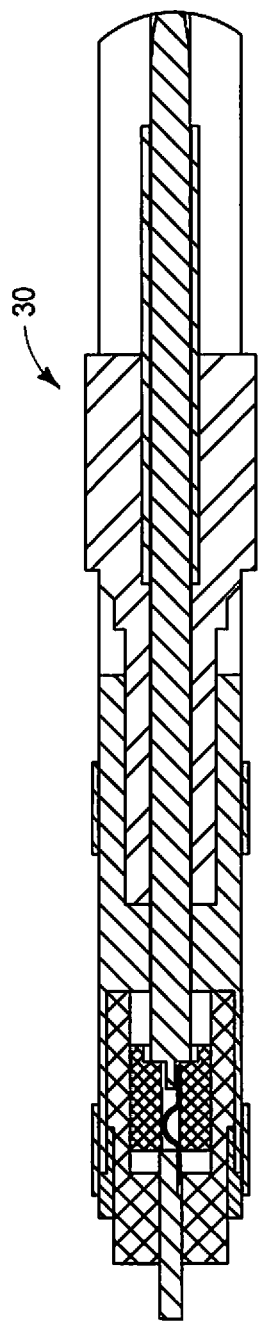
FIG. 12 is an enlarged cross section view of the EFP probe of FIG. 11.

A coaxial cable 75 is electronically coupled with the conductor weld pad 71 so that signals may be transmitted to the probe 30 and received from the probe 30. As shown in FIG. 9, the coaxial cable 75, and its attachment to the conductor weld pad 71, is positionally secured to the probe body 31 by an inner slip support 69, a pack 73 and a ring 74 so that the coaxial cable 75 is securely, and insulatively connected to the center conductor 60. In the current embodiment the pack 73 and ring 74 are formed of TEFLON®, but other materials such as PEEK® may similarly be used and are contemplated. Plural support straps 72 further secure the coaxial cable 75 connections relative to the probe 30.

The coaxial cable 75 that electronically communicates with the EFP probe 30 is electronically coupled with a pulse emitter 120 and also with pulse sampler 150. The pulse emitter 120 and the pulse sampler 150 may also be combined into a single apparatus/unit commonly called a Time Domain Reflectometer (TDR), such as the EFP Signal Processor utilizing the CT100B software developed and manufactured by Mohr Test and Measurement of Richland, Wash., USA. Such TDR EFP Signal Processors are described in U.S. Pat. No. 4,786,857 issued Nov. 22, 1998, and U.S. Pat. No. 5,723,979 issued Mar. 3, 1998, and U.S. Pat. No. 6,144,211 issued Nov. 7, 2000, and U.S. Pat. No. 6,348,803 issued Feb. 19, 2002 and which were all invented by Charles L. Mohr (one of the joint inventors herein). The aforementioned issued U.S. patents and the teachings therein are expressly incorporated herein by this reference.

As shown in FIG. 20, when the system is fixed, or otherwise permanently or semi-permanently plumbed into/interconnected with a fluid 14 movement system/apparatus of a drilling rig, one or more grayloc supports 80 may be used to positionally secure the EFP probe(s) 30 in position. A grayloc support 80 (FIG. 20) is a pipe fitting having a "cross" configuration defining an entry port 81, an exit port 82, a probe insertion port 83 and a blind port 84. Each of the ports 81, 82, 83, 84 communicate with a medial chamber 85 therebetween to allow fluid flow therethrough. An exterior circumference of each port 81, 82, 83, 84 defines a radially enlarged sealing flange 86 configured for engagement with a two-part sealing clamp (not shown) to provide a fluid tight seal between the grayloc support 80 and the adjoining pipe 20, or an adjoining hub (not shown) to provide fluid containment. An active end support 77 frictionally engages the first end 32 of the probe 30 and extends over and about the coaxial cable 75 and an inner slip support 69. The active end support 77 aligns and positionally maintains the first end 32 of the probe body 31. A passive end support 78 frictionally engages with the second end 33 of the EFP probe 30 and similarly aligns and positionally maintains the second end 33 of the EFP probe 30 relative to the grayloc support 80, the medial chamber 85 and the fluid 14 flowing therethrough.

In one contemplated embodiment plural grayloc supports 80 may be interconnected with a pipe 20 a known distance from one another and each grayloc support 80 may carry an EFP probe 30, one probe 30 within each grayloc support 80. The first probe 30 and the second probe 30 may be identical in configuration and function. These two spaced apart grayloc supports 80 each carrying an EFP probe 30 allows the present method and apparatus to also calculate/determine velocity and volume to be calculated without use of a flow meter 90.

Time domain reflectometry is known as an effective means for determining the level of a liquid 14, such as in a tank, or reservoir 135. Using time domain reflectometry, electrical pulses are conveyed along a transmission line, which may be a coaxial cable 75, to the electrically conductive EFP probe 30. The electrical pulses are partially reflected when there is a change in the electrical impedance of the fluid 14 to which the EFP probe 30 is exposed. The impedance change is associated with a difference in dielectric strength. "Electrical permittivity" is a technical term indicating the dielectric properties of the fluid 14. The electrical pulses produced by a time domain reflectometry system are affected by the dielectric constant of the surrounding fluid 14 in which the electrical pulse is traveling. The dielectric constant (permittivity) of the fluid 14 directly affects the propagation velocity of an electromagnetic wave as it travels along the probe 30. In time domain reflectometry systems, an electromagnetic pulse is propagated into and along the EFP probe 30 which has a known length while measuring the time of arrival and the time of reflection from electrical discontinuities at two known, spaced apart, points. The first known point is where a coaxial cable 75 is attached to the EFP probe 30. The second known spaced apart point, is a distal end of the EFP probe 30. Since these locations are both known, one can electromagnetic wave and, as a result, calculate the apparent dielectric constant of the material undergoing tests and to which the EFP probe 30 is exposed. Similarly, changes in the dielectric constant which relate to changes in the fluid 14 adjacent to and surrounding the EFP probe 30 can also be determined. For example, the apparent dielectric constant provides a direct indication of the presence of identifiable types of fluids 14, such as, but not limited to, oil 15 and water 16, and various volume fractions of the fluid 14 calculate the propagation velocity of the The pulse emitter 120 which may be incorporated into a TDR is an electronic apparatus that emits electronic pulses (not shown) which are conveyed to the EFP probe 30 through the coaxial cable 75 at a preferred rate of approximately 500 to 800 samples per second depending upon the speed of computation and generating approximately 500 data points per sample. This means the electronic pulses are at increments of approximately 0.76 picoseconds. When the pulse emitter 120 emits a pulse (not shown) the pulse is conveyed along the coaxial cable 75 and to the EFP probe 30 center conductor 60 through the conductor weld pad 71. The pulse travels along the center conductor 60 whereupon, depending upon the constituents 15, 16, 17 of the surrounding fluid 14 and the respective impedance (dielectric constants) of the constituents 15, 16, 17 to which the EFP probe 30 is exposed, an electrical pulse reflection (not shown) is created when the pulse experiences a change in velocity due to a change in electrical impedance caused by a change in dielectric constant of the fluid 14 within the probe gaps 66 and surrounding the EFP probe 30 active area. The pulse reflection is received from the EFP probe 30 through the coaxial cable 75 and is communicated to the pulse sampler 150 where the reflection is sensed and recorded.

As the dielectric constant properties of the fluid 14 constituents 15, 16, 17 surrounding the EFP probe 30 and within the probe gaps 66 change due to changing constituents 15, 16, 17, the velocity and distance traveled by the pulse in the increment of time between any two sequential pulses changes the apparent length of the EFP probe 30. The pulse reflection, which indicates the end of the EFP probe 30 or impedance change (the length of the probe in time), is conveyed along the coaxial cable 75 to the pulse sampler 150. Known computer logic within the controller/computer 170 which is in electronic communication with the pulse emitter 120 and the pulse sampler 150 calculates the "length of the probe in time." Determination of the "length of the probe in time" is empirically representative of the dielectric constant of the fluid constituent 15, 16, 17.

The controller/computer 170 has a database 172, which has stored therein, data and information on predetermined known dielectric constants and permittivity curves of the fluid constituents 15, 16, 17 and predetermined time delays generated by various dielectric constants. The database 172 also has stored therein predetermined known data and information of resonance points of various known volume fraction constituents 15, 16, 17 and the resonance points of various concentrations of the volume fraction constituents 15, 16, 17. The database 172 may also be a correlation or an algorithm wherein information may be correlated and/or compared.

The controller/computer 170 determines the time difference between emission of the electrical pulse into the EFP probe 30 by the pulse emitter 120, and receipt of the pulse reflection from the EFP probe 30, by the pulse sampler 150. The determined time is then correlated by the controller/computer 170, using the database 172 to known predetermined dielectric constants of known volume fraction constituents 15, 16, 17 which would similarly generate the determined time difference. The correlation of the determined time difference with information contained within the database 172 permits identification of the volume fraction constituent 15, 16, 17 fluid 14 by "matching" the determined time difference, with the predetermined known dielectric constant of various known constituents 15, 16, 17 of the fluid 14 which allows identification of the volume fraction constituent 15, 16, 17.

The determined time difference between the electrical pulse emission from the pulse emitter 120 into the EFP probe 30, and receipt of the electrical pulse reflection from the EFP probe 30 by the pulse sampler 150 provides a "length of the probe" measurement which is shared with a detection algorithm within the controller/computer 170 that compares the known "length of the probe" (which correlates to the impedance of the probe 30) to known dielectric constants, which may vary with salt content, and temperature as detected by the temperature sensor 100 in order to match the determined parameters with a known baseline to identify the volume fraction constituents 15, 16, 17 within the fluid 14. This first measure is time domain evaluation. It is the behavior of the electrical pulse within the EFP probe 30, and the resulting length of the probe 30 which allows a first identification of the fluid constituents 15, 16, 17. As the fluid 14 passes around and about the EFP probe 30 and through the gaps 66 between the center conductor 60 and proximate edges of the ground plates 40, 50, the pulse reflection, received by the pulse sampler 150 changes as the volume fraction constituents 14, 15, 16 of the fluid 14 change. The change is caused by the changing electrical impedance and changing dielectric constant of the fluid 14 that is in contact with the EFP probe 30 and immediately surrounding the EFP probe 30.

In a second contemplated configuration (FIG. 19) the EFP probe 30 has an extension tail 76, which may be a length of coaxial cable, that is electrically coupled with the second end 33 of the EFP probe 30 body 31 and center conductor 60 so that electrical signals transmitted to the EFP probe 30 passes completely through the probe 30 and into the extension tail 76 and along the length of the extension tail 76 before generating a reflection signal at the terminal end of the extension tail 76. The added length of the extension tail 76 "delays" the reflection signal so that there is greater contrast in the probe signals which provides a greater ability to differentiate the signals generated by the dielectric constants of the constituents 15, 16, 17 and the reflection signal.

The length of the extension tail 76 is usually four times the length of the EFP probe 30 but can be as long as eight times the length of the EFP probe 30. The EFP probe 30 is preferably about 2.7 inches in length so the length of the extension tail 76 may be approximately ten inches up to approximately twenty-two inches. The object is that the determined reflection time period would not interfere with the signal at the end of the EFP probe 30. The extension tail 76 allows measuring of the frequency components more accurately and will preferably be used both in evaluating fluids 14 including, but not limited to, drilling fluids and also with multi-phase systems where gases and gaseous fluids may be present.

In a third contemplated probe configuration (FIGS. 16, 17) the EFP probe 30 is a "through probe" design such that there is no reflection signal generated by a terminal end of the probe 30 or terminal end of an extension tail 76. Rather, a length of coaxial cable 75 has a first end that is electrically interconnected with the second end 33 of the probe 30 and center conductor 60 and the coaxial cable 75 has a second opposing end (not shown) that is electrically interconnected with the pulse sampler 150 which effectively creates an "endless loop" which prevents the creation of any "reflection signal". The "through probe" configuration (FIGS. 16, 17) has the added benefit of enhancing contrast and further lengthening the signal to provide enhanced ability to evaluate the resonance points and permittivity curve of the constituents 15, 16, 17 surrounding the EFP probe 30.

The third contemplated configuration of the EFP Probe 30 requires use of a two port TDR (not shown) having one port that one sends the signal and the other port receives the signal so that and the reflected signal confusion is removed. A dual port system (not shown) allows determination of phase relationships and the complex permittivity (real and imaginary) terms better than using the reflected single port system including more subtle variations in the materials being examined.

For the blade probe 30 design (FIGS. 9-12) and the extended tail 76 design (FIG. 19) the reflected signal travels back to the pulse sampler 150 as the sampled reflection. For the dual port system (not shown) the signal, now modified by the double ended probe 30 is sampled at the second TDR with no signal reflected and is measured at the driver end.

However, it is also known that the dielectric constants of such volume fraction constituents 15, 16, 17 are variable and dependent upon temperature and salt content and therefore using only one measure does not generate consistently reliably accurate results.

A second, frequency domain evaluation takes advantage of the resonance of an electrical signal in the fluid 14 and provides another method of identifying the volume fractions in the fluid 14 and also allows measuring of a concentration of the volume fraction constituent 15, 16, 17 within the fluid 14. By performing a Fast Fourier Transform (FFT) of the previously determined time delay of the pulse reflection, a sine wave frequency is determined. The frequency and amplitude of the sine wave signal (Power Spectral Density PSD) allows different characteristic patterns of the constituents 15, 16, 17 to be identified. By examining the various resonance points as the frequency increases, the distance between the resonance points and the amplitude (strength) of the resonance points provide additional information as to various volume fraction constituents 15, 16, 17 within the fluid 14 and allows identification and characterization of those various volume fraction constituents, such as drilling fluids, drilling mud 17, oil 15, water 16, natural gas and other components which may be newly appearing in the fluid 14 and surrounding the probe 30. A shift in resonance allows a measure of the fraction of each of the volume fraction constituents 15, 16, 17.

By performing the Fast Fourier Transform (FFT) of the reflected electrical pulse received by the pulse sampler 150, and by performing a Power Spectral Density (PSD) calculation, the frequency and amplitude of the resonance points can be identified.

The FFT takes a time-based plot (the determined time delay) and converts the time-based plot into a series of sine waves that duplicate the time history of the electric pulse as a series of frequency based sine waves with the maximums and minimums of the sine waves representing amplitude and resonance points of the volume fraction constituents 15, 16, 17 to which the probe 30 is exposed during the pulse and reflection thereof. The PSD calculation determines the average power, amplitude and frequency of the FFT transform. The first resonance point is identifiable because it has a wavelength that is equal to twice the active length of the probe 30.

The relative permittivity of the fluid 14 is calculated by comparing the determined velocity of the signal while the EFP Probe 30 is immersed in the fluid 14 constituents 15, 16, 17 to the velocity of light in a vacuum using the following relationship between velocity and dielectric:

$$\frac{cf}{c} = \sqrt{1/ef};$$

where cf is the transmission speed of the pulse in the fluid 14, c is the speed of light in a vacuum, and ef is the relative permittivity or dielectric constant of the fluid 14. It is further noted that an inverse of the FFT allows recreation of the time history plot.

The time domain evaluation, and the frequency domain evaluation, provide two separate methods to identify volume fraction constituents 15, 16, 17 in the fluid 14 and further allows a determination of a concentration of each volume fraction constituent 15, 16, 17 to be determined. The frequency domain evaluation further allows the concentration of the various volume fraction constituents 15, 16, 17 in the fluid 14 to be determined by correlating the resonance points of the fluid constituents with known resonance points of known constituent concentrations within the database 172.

As noted previously, the drilling of an oil or gas well requires a multi-component drilling fluid 17 which is injected into the boring head of the drill string 140 to lubricate the drill bit, carry effluent to the surface, support the well bore and prevent pressurized gas from escaping the well bore 138 and causing a "kick" or blow-out of the well.

Drilling fluid 17 is a complex fluid of oil-based or aqueous-based mixtures. Large tanks are used to mix, store, filter and recirculate the drilling fluid 17 during drilling operations. Commonly a mixing/suction tank 135, is the location where the drilling fluid 17 is suctioned from, pumped to the top of the drill string 140 by high-pressure pumps 136, and injected into the well bore 138. The drilling fluid 17 displaces the existing fluid, which is circulated "regurgitated" back to the surface as "return fluid" where the return fluid is diverted onto a shaker 131, which removes the large rocks and debris from the return fluid. Then on to discharge/settling tanks 132 where a percentage of the return fluid 14 is transferred to a centrifuge 133 to remove the majority of the rock, sand and debris and then mixed with additional drilling fluid 17 for pumping back into the well drilling operation.

One primary safety assessment tool for well drilling operations is to correlate the volume of return fluid 14 returning out of the hole 138 with the volume of fluid 14 being pumped back in the hole 138, the density of the return fluid 14 coming out of the hole and the density of the drilling fluid 17 being pumped back down the hole 138. The oil/water fraction provides a measure of the dilution of the drilling fluid 17 and that measure combined with density forms the basis for the safety assessment of the operation of the well drilling operation as a first approximation of what needs to be added to the drilling fluid 17 to maintain density and fluid chemistry.

During recirculation in the well bore 138, the drilling fluid 17 can become diluted with ground water or other liquids, or altered chemically by naturally occurring substances. Continuous monitoring of the drilling fluid 17 and return fluid is essential to the successful completion of a well drilling operation as it prevents binding of the drill head, and prevents "kicks" or "blow-outs" of the well. During a "kick" or blow-out, the possibility of explosion and fire is likely, which can be deadly to the workers and cause extensive damage to the drilling equipment.

Our EFP Drilling Fluid Measurement system is used to characterize several in-situ, real time parameters of drilling fluid 17 and return fluid including, but not limited to: density, temperature, and oil/water ratio. These measures coupled with existing laboratory techniques to calibrate the process where the other drilling fluid parameters are measured provides a clear path for control of the drilling process and to maintain safety margins. The instant inventive EFP system provides near real time measurement of the parameters directly related to drilling safety. The instruments are designed to be portable, but may also be a fixed part of the drilling process and plumbed into the piping system where it would be coupled with a flow meter 90 system for measuring both return flow and, on the pressure side providing high pressure drilling fluid 17 to the drill string 140.

The instant method and apparatus increases the safety, reliability and effectiveness of a drilling operation. Current methods utilize a series of labor intensive tests by a trained drilling fluids engineer. The tests may include slump funnels, precision scales, and distilling or other laboratory testing for accurate density and water cut measurements, viscosity and other chemical test. These measurements may be taken only once a day or a few times per day. Our EFP system complements these labor intensive tests with simple measurements that can be taken continuously throughout the operation, providing real-time feedback for adjusting the fluid constituents of the drilling fluid 17.

Our Portable EFP Drilling Fluid Measurement System is a battery-operated portable instrument that utilizes separable probes (Density probe and EFP probe) immersed into the drilling fluid to determine the parameters of the fluid.

The Electronic Enclosure 300 (FIG. 2) is a sealed, portable enclosure that contains all of the system electronics required to drive and read the sensors mounted on the separable probes 41, 180 that are operated one at a time. There is a touch screen visual display 200 for operation of the unit and an external Wi-Fi connection for control by an operator interface.

The Density Probe 180 (FIGS. 5-8) has an elongated support 184 having a handle 185 at a handle end, and an opposing distal end 186 opposite the handle 185. Two highly sensitive pressure transducers 181, 182, of known construction, are separated by a known distance 183 on the elongated support 184. A temperature sensor 100 is also carried on the elongated support 184 and is used for temperature compensation of the readings. The two pressure transducers 181, 182 of the density probe 180 are submerged to a depth below the surface of the fluid 14. (See FIG. 18). The pressure differential between the two pressure transducers 181, 182, in conjunction with the fluid temperature is used to calculate the density of the fluid 14. Control buttons 187 located on the handle 185 actuate the measurement process of taking temperature and also to take the delta pressure measurement.

Figure 15:
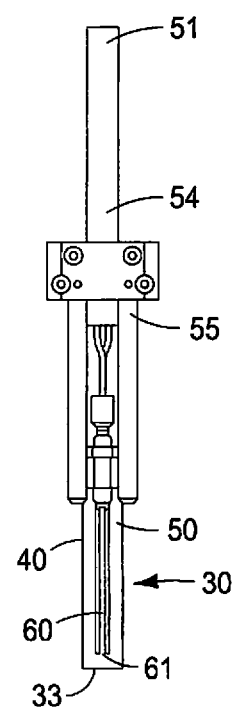
FIG. 15 is an enlarged orthographic front view of the EFP probe of FIG. 14.

The portable EFP Probe 41 (FIGS. 14-15) has an elongated support having a handle 52 at a handle end, and an opposing distal end 54 opposite the handle 52. The EFP probe 30 is carried at the distal end 54 by probe support assembly 55 the electrically isolates the EFP probe 30 from the elongated support. Control buttons (not shown) incorporated into the handle 52 allow an operator to actuate the testing/measuring process. The coaxial cable 75 that communicates with the EFP probe 30 is supported by the elongated support. As shown in FIG. 18, the portable EFP probe 41 configuration allows an operator to immerse the EFP probe 30 within the fluid 14.

The controller/computer 170 is used to provide full data transfer and communicates with the Electronics Enclosure 300 to display results of the measurements or perform more complex analysis of the data.

Figure 2:
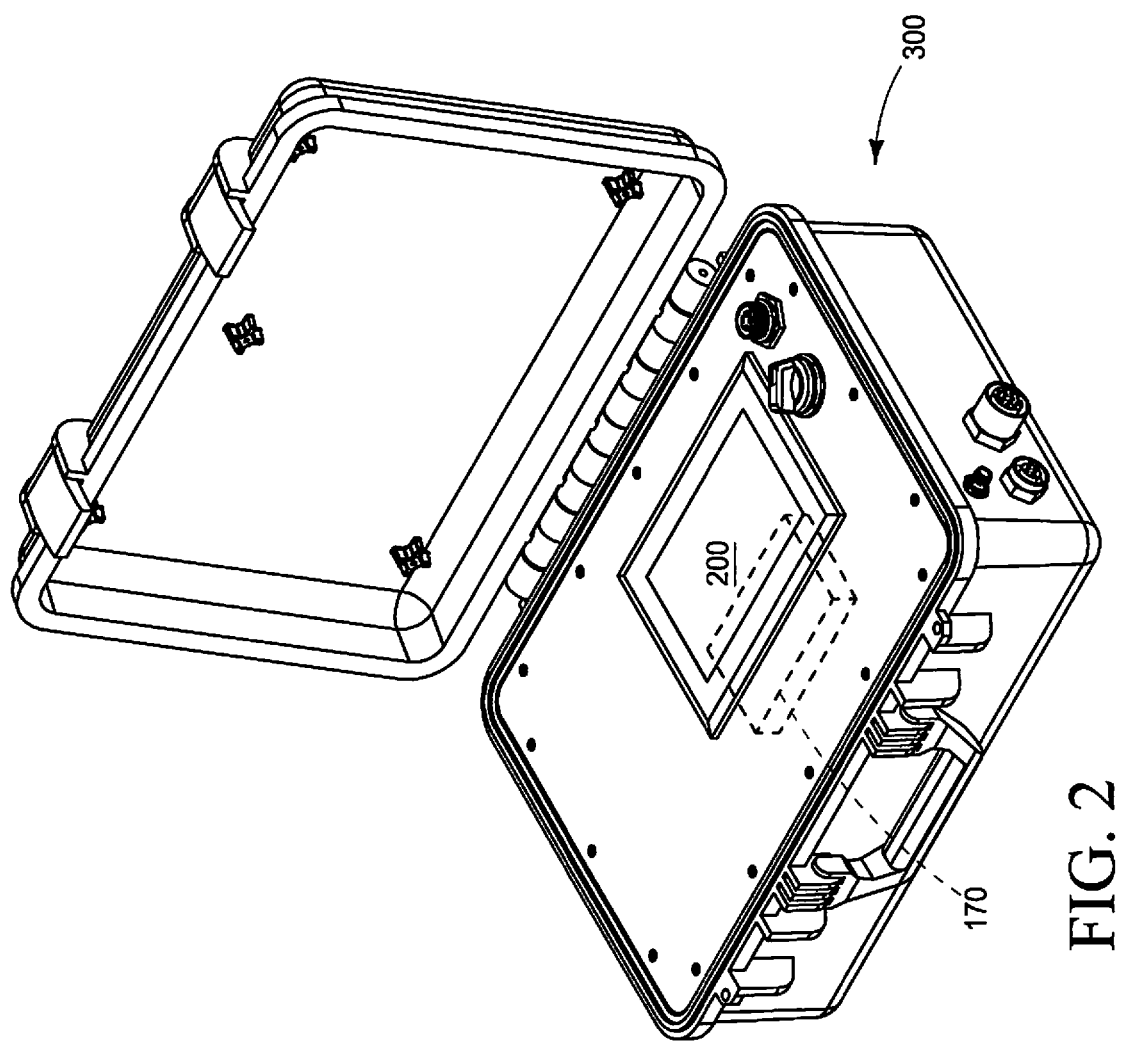
FIG. 2 is an isometric front top and side view of the electronics enclosure and controller/computer.
Figure 3:
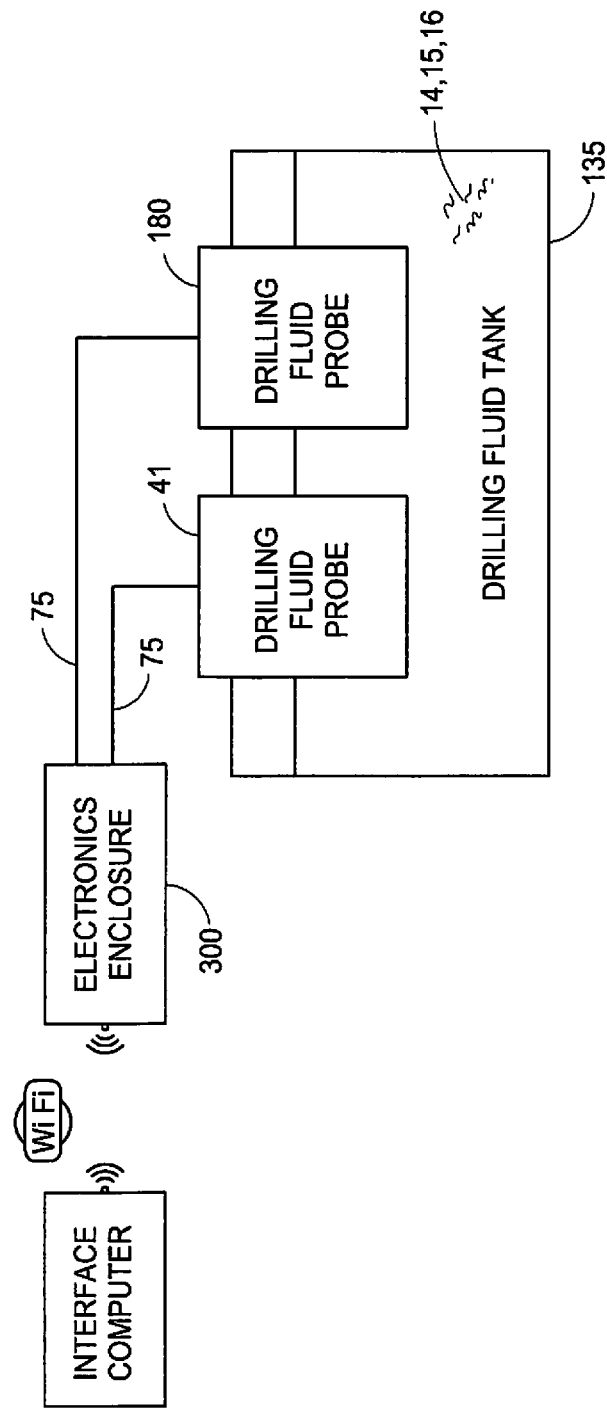
FIG. 3 is a generalized block diagram of the components communicating wirelessly.
Figure 4:
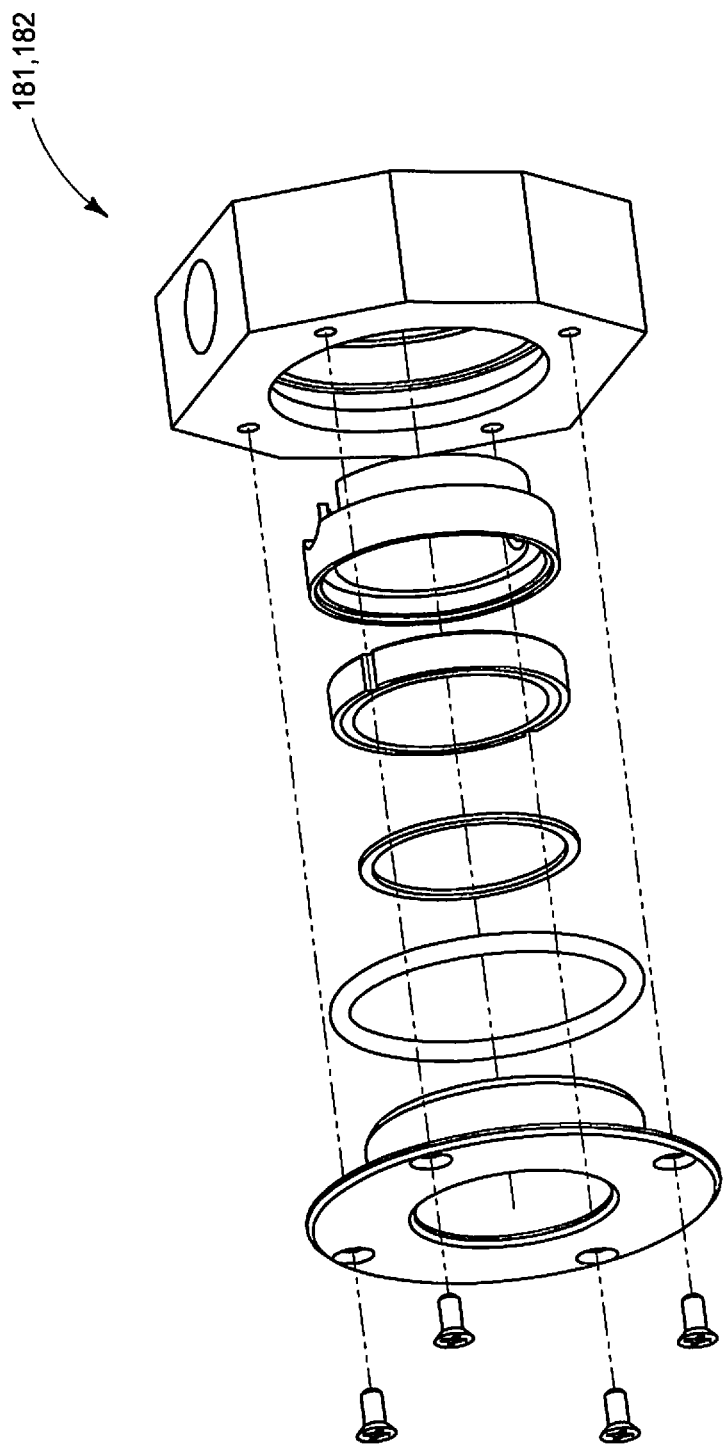
FIG. 4 is an isometric exploded view of a pressure density probe transducer.

As shown in FIGS. 2 and 3, the controller/computer 170 is enclosed in a case that meets Class I Division II Group C& D Splash proof designation. The sensors that are attached by electrical cables are Class I Division I Groups C&D Intrinsically Safe Submersible. The visual display 200 may have a touch screen interface on the front panel in the Electronics Enclosure 300 that allows communication with the operator and control of the operation of the unit. Down load of all measurements and identification of samples etc. can be accomplished via Wi Fi to the intrinsically safe interface computer.

The current invention provides a Portable Fluid Measurement System. The instant invention and, system electronics may also be utilized in a fixed placement application. In this application the EFP Drilling Fluid Probe 30 is mounted at a fixed location in the drilling fluid support equipment, such as in a grayloc support 80 plumbed into the pipes 20 and the fluid system.

Measurements of the dielectric constant of the fluid 14, the density of the fluid 14 and the temperature of the fluid 14 allows characterization of the volume, the density, and the water content of the drilling fluid 17 flowing into the well, and out of the well. The addition of the flow meter 90 may require additional laboratory data to allow the flow meter results to be corrected for viscosity for absolute flow to be calculated.

The density measurements are preferably taken downstream of the sieve/shaker 131 and flow meter 90 and within the discharge/settling tank 132. This measurement location offers more protection to the density probe 180 from the rocks and debris associated with the return fluid.

The use of multiple measurement locations will provide volume/rate data to determine the dynamic change in inventory of drilling fluid 17 and the transient change in flow. This provides additional safety information from which density/dilution of the drilling fluid 17 in the well is determined.

Use of a flow meter 90 is not required, but increases the available data for the Drilling Fluid engineer, allowing calculation of both the dilution of the fluid 14 and the physical volume of fluid 14 being lost to process issues or underground cavities. In some cases, laboratory data will be needed to provide chemistry data.

Figure 1:
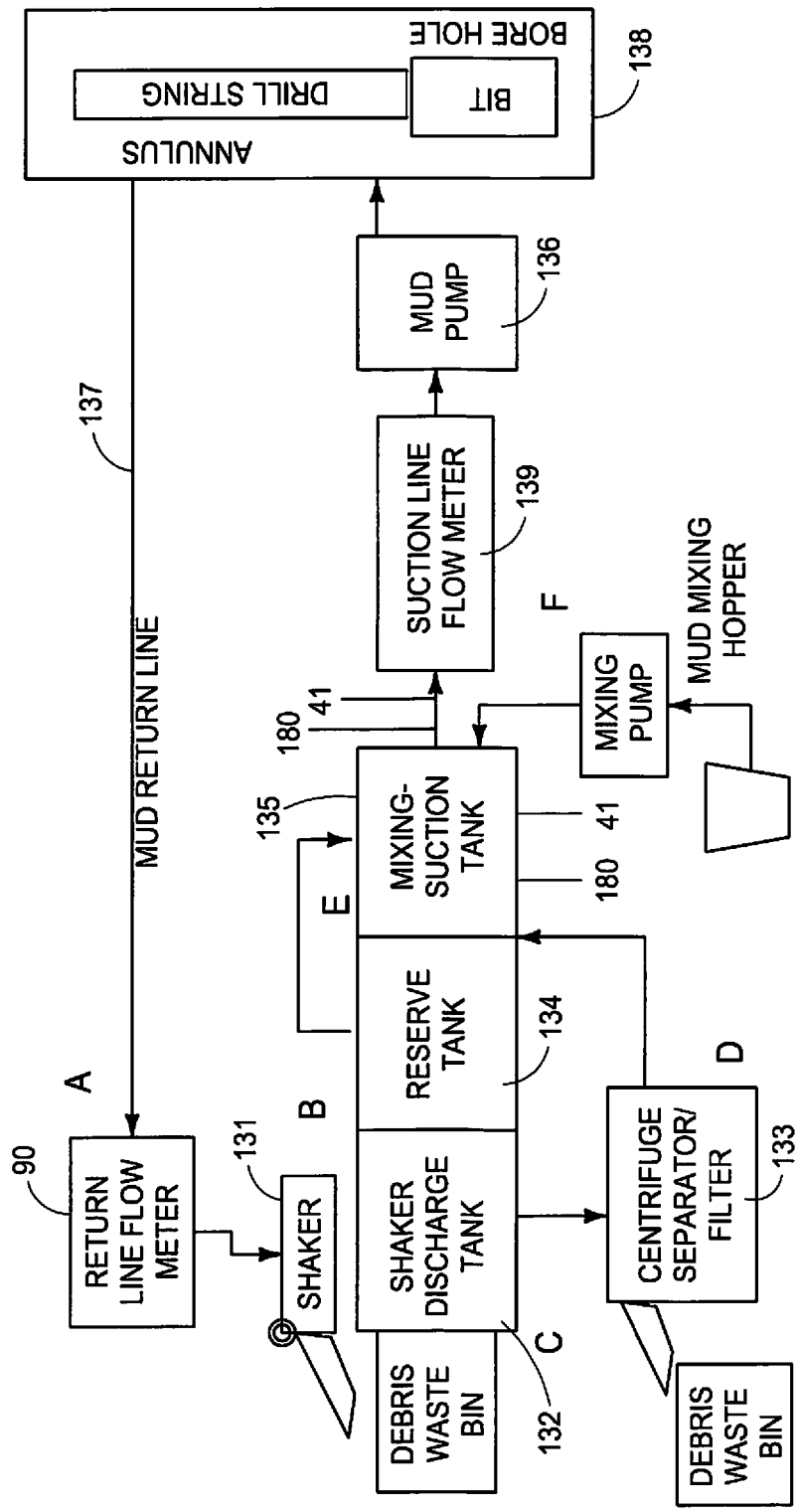
FIG. 1 is a generalized block diagram showing arrangement of the various components of a drilling rig system, and fluid flow therethrough, and showing possible placement of the temporary and permanent measurement taking locations.

A common/typical drilling system is shown in block diagram in FIG. 1. This generic flow diagram with system components is typical of a drilling operation and is shown for clarity and basic information of where measurements may be made.

The borehole 138 is defined in the ground and the drill string 140 (composed of interconnected segments of drill pipe and a drill bit) extends into the borehole 138. Return fluid 14 comes out to of the borehole 138 exterior to the drill string 140, and the return fluid 14 is carried in the mud return line 137 which may have a flow meter 90 to measure and determine the amount of return fluid 14 being returned from the borehole 138. The regurgitated fluid 14 is thereafter processed for reuse, but is first subjected to various measurements and analysis to determine the volume fractions and component makeup of the fluid 14.

Shaker 131 separates rocks and debris from the returning fluid 14.

A discharge tank 132 proximate below the shaker 131 removes sand and other debris not removed by the shaker 131. Return fluid 14 is taken from the discharge tank 132 and sent to the Centrifuge 133 to remove sand and other debris not removed by the shaker 131.

The centrifuge 133 receives approximately ⅓ of the return fluid and processes the return fluid 14 through an extraction process to remove as much sand and fine particles as possible. The output is returned to the either the reserve tank 134 or mixing/Suction Tank 135.

The Reserve Tank 134 is used to take overflow and allow further settling and mixing of make-up materials and correcting water content and chemical changes that are needed.

The mixing/Suction Tank 135 receives the return fluid 14 from Centrifuge 133 and input from Reserve Tank 134 to adjust fluid chemistry. In the mixing/suction tank 135 a density probe 180 may be permanently installed, or temporarily immersed, to measure Density corrected by Temperature. It is also in the mixing/suction tank 135 that the EFP probe 30 measurements may be taken using the portable system 41 (FIG. 14) which allows the EFP probe 30 carried at the distal end 54 of the elongated support 51 to be temporarily immersed in the fluid 14 within the tank 135.

In the installation of a permanent system (not shown), to perform the measurements, both the EFP probe 30 and the density probe 180 may be plumbed (permanently interconnected) such as within the suction line 139, or other pipe 20 so as to take measurements of the fluid 14 in the pipe 20.

As shown in FIG. 18, the preferred embodiment of the invention is portable wherein both the portable EFP probe 41 carrying the EFP probe 30, and the density probe 180 carrying the two pressure transducers 181, 182 are immersed in the fluid 14 within the mixing tank 35, and the portable EFP probe 41 and the density probe 180 electronically communicate with the electronics enclosure 300.

FIG. 21 shows the measurements of two groups of drilling fluids showing results of the EFP probe 30 spectroscopy (the EFP Signal) compared with the measured water content in % by volume. FIG. 21 shows that the signal over the range of data is well presented and easy to determine the water fraction in drilling fluid 17 samples.

A complex permittivity curve describes the electrical permittivity of a material and is a property of the material independent of the current inventive EFP method and system.

A complex permittivity curve is a function that takes frequency as input and returns the electrical permittivity that would be measured if the material were exposed to an electrical pulse at the given frequency.

The permittivity at a given frequency has a lossless component, which is the real value of the permittivity, and a lossy component, which is an imaginary part of the permittivity. Added together, these two components make the complex permittivity for the material at the given frequency.

The complex permittivity curve describes the complex permittivity values for a range of frequencies.

Complex permittivity is related to the concept of Dielectric Constant. The dielectric constant of a material is equal to the complex permittivity of the material at DC (0 Hz) frequency, divided by the permittivity of the vacuum. Since there is never any lossy permittivity at 0 Hz, Complex Dielectric is always a real value.

A complex permittivity curve for a given material may change with density and temperature.

All materials have electrical permittivity. Oil and Water have distinct complex permittivity curves at any density and temperature encountered in drilling and extraction operations. A measured complex permittivity curve for an oil-water mixture can be used to determine the oil-water ratio.

Complex permittivity for a mixture can be calculated from the scattering parameters (S11, S21) of the EFP probe 30 that is immersed in the fluid mixture. The scattering parameters of the EFP probe 30 are a function of the probe geometry and the complex permittivity of the fluid 14 that surrounds the EFP probe 30. Therefore, knowing the EFP probe 30 geometry and the scattering parameters is sufficient to make an estimate of the complex permittivity of the fluid 14.

The instant method and system provides a database 172 of complex permittivity curves for oil 15 and water 16 at a range of temperatures and densities.

Scattering parameters are a representation of a passive electrical component, such as an EFP probe 30. A complete set of scattering parameters completely describes the electrical behavior of the component.

An electrical component will have some number of electrical connections to the rest of the circuit, commonly called "ports" when dealing with scattering parameters. In the case of a single-ended EFP probe 30, there is only one port. (See FIGS. 9-12). In a dual-ended or "through" EFP probe 30 there are two ports. (See FIGS. 16-19).

A scattering parameter is a description of the relationship between input on a port to output, on the same, or different port. The ports are arbitrarily assigned a number. The parameter S11 gives the relation between the input on port 1 with the output on port 1. The parameter S21 gives the relation between the input on port 1 and the output on port 2.

To completely electrically describe a single port probe, an S11 is sufficient. To completely electrically describe a dual port probe, four scattering parameters make a complete set: S11, S21, S12 and S22. Because a dual ended probe is symmetrical, an assumption is made that S11 and S22 are identical, and S12 and S21 are identical, so that S11 and S21 only need to be calculated.

The S11 parameter is directly derived from the measured reflected signal from the EFP probe 30, while the S21 is directly derived from the measured transmitted signal through the probe 30.

There are different equivalent representations of scattering parameters. One representation is as a time-domain response trace for a unit electric impulse. Another is as a frequency domain specification of gain and phase shift for inputs at given frequencies. The latter is the representation used in the present inventive method, but again, the two are equivalent.

When represented in the frequency domain, the scattering parameter is a complex number, with the amplitude giving the gain from input to output, and the phase angle of the value matching the phase shift of the output relative to the input. The amplitude of the S11 is also called the Return Loss of the component, and the amplitude of the S21 is the Insertion Loss of the component.

When the scattering parameters are known, and the input signals are known, the output signals can be calculated by convolving the input signals with the scattering parameters.

With the EFP probe 30, the input signal is known by calibration of the pulse emitter 120, and the output is measured. The scattering parameter can then be calculated by de-convolving the input signal from the output signal.

The design of the EFP probe 30 ensures that the scattering parameters of the probe 30 are predictably related to the complex permittivity of the fluid 14 in which the EFP probe 30 is immersed it is submerged.

Scattering parameters are not properties of the fluid 14, but electrical properties of the EFP probe 30 that can be used to calculate a complex permittivity curve of the fluid 14. Oil 15 and water 16 do not have scattering parameters. However, the scattering parameters of the EFP probe 30 are significantly different when immersed in oil 15 or water 16.

FIG. 22 shows a graph of two measurements of an S11 scattering parameter of a cable in the frequency domain. The two measurements were taken with two different instruments.

Like scattering parameters, resonance points are an electrical property of the EFP probe 30. They are not a property of the fluid 14. Oil 15 and water 16 do not have resonance points.

The EFP probe 30 is designed so that its resonance points are significantly different when immersed in oil 15 versus when immersed in water 16.

Resonance points are frequencies which resonate with the EFP probe 30. Resonance points are near integer or half-integer (1.5, 2.5) multiples of some lowest frequency. The small deviations from one resonance point to the next can be used to estimate the amplitude of the complex permittivity at the frequency of the resonance points.

Resonance points can be found and measured from a EFP reflected or transmitted signal by analysis of the signal transformed to the frequency domain using a Fast Fourier Transform (FFT).

FIG. 24 shows three resonance points of an EFP probe 30 in water 16. As shown, the resonance points are approximately at half-integer multiples of 240 MHz, with some deviation.

FIG. 23 shows resonance points for the EFP probe 30 in two kinds of oil 15 and air, as well as water 16. The resonance points in air are higher frequency than those in oil 15, which are much higher frequency than the resonance points in water 16.

The exact frequency of a resonance point, plus its multiple (1×, 2×, ... ) or (1.5×, 2.5×, ... ) is sufficient to calculate the amplitude of the permittivity at that frequency.

FIG. 24 shows resonance points on a frequency domain representation of a reflection from an EFP probe 30 submerged in water 16. The resonance points are the downward spikes in the graph. Note that the resonance points are near half-integer multiples of about 240 MHz Three techniques are used to calculate dielectric constant and complex permittivity.

Each technique is more powerful, but more complicated than the one before and each technique can be used simultaneously on the same EFP signal.

The terms Dielectric Constant and Permittivity are related, and to some extent, are the same thing. The dielectric constant is also called the Relative Permittivity. For a material, the relative permittivity is the ratio between the absolute permittivity of the material and the permittivity of free space.

Relative permittivity can be measured by measuring the capacitance between two plates with the material to be measured in between the two plates. The higher the dielectric, the higher the capacitance.

For an AC signal, the permittivity of a material typically varies between frequencies. The dielectric constant, is the relative permittivity at 0 Hz and does not relate to the electrical properties of the material at higher frequencies.

In addition, with an AC signal, energy can be lost to the material. The combination of the loss-less component and the lossy component of electrical permittivity is represented as a complex number, with the lossy component as the imaginary term.

The speed of the pulse through the EFP probe 30 is inversely related to the dielectric constant of the fluid 14 surrounding the EFP probe 30. As the dielectric constant changes, the time for an electric pulse to leave the pulse emitter 120 and return to the pulse sampler 150 will also change.

FIG. 25 is a graph of the dielectric constant of two similar, oil-based drilling fluids, showing the "mud_2a_21 graph" representing a drilling fluid that has a higher percentage of water 16 than the "mud_1A_21 graph". The "mud_2a_21 graph has a higher dielectric constant, which slows the pulse through the EFP probe 30 slightly, and leads to a delay in the return signal to the EFP/pulse sampler 150.

The result of this measurement is a measurement of a single dielectric constant for the fluid 14 mixture which surrounds the probe 30.

If a sine wave of a single frequency were sent continuously from the EFP/pulse emitter 120 to the EFP probe 30, the wave would reflect from two places: the start 62 of the EFP probe 30 and the end 61 of the EFP probe 30. (See FIG. 26) The reflections would be sine waves of the same frequency.

The reflected sine waves add together and appear as a single sine wave at the EFP pulse sampler 150. At certain frequencies, the reflecting waves will cancel each other out. This phenomenon is known as destructive interference. At these destructive frequencies, the apparent amplitude of the reflected pulse drops suddenly.

These frequencies are the resonance points. The resonance points appear as sharp downward spikes in Frequency domain plots of the probe signal. See FIG. 24.

By analysis, the wavelength of the pulse at the resonance points are always equal to twice the length of the EFP probe 30 divided by an integer (1, 2, 3 . . . ), or divided by a half-integer (½, 1½, 2½, . . . ). The exact divisor can be found by counting resonance points.

The wavelength of an electric pulse at a given frequency is a function of the speed of the pulse. The speed of the pulse is inversely related to the permittivity at that frequency. From the divisor of a resonance point the wavelength may be calculated. From the wavelength and the frequency speed may be calculated, and then permittivity.

Because the resonance point technique is a single frequency measurement, the frequency dependent permittivity may be calculated. Because there are multiple resonance points the permittivity is calculable at a number of different frequencies.

OPERATION

Having described the method and apparatus for measuring and characterizing multiple parameters of drilling fluid, its operation may be understood.

A source of fluid 13 is provided, the source of fluid 13 providing fluid 14 having a volume fraction of water 16 and a volume fraction of oil 15, and wherein the volume fractions of water 16 and of oil 15 each have a previously determined and known complex permittivity curve.

Providing a database 172 having stored accessible information about the previously determined and known complex permittivity curve of the volume fractions of water 16 and of oil 15.

Providing a temperature probe 180 exposed to the fluid 14 to determine the temperature of the fluid 14.

Providing a portable electric field perturbation (EFP) probe 41 having a handle 52 at one end and carrying a probe support assembly 55 opposite the handle 52 and the probe support assembly 55 carries an EFP probe 30 that is electronically isolated from the probe support assembly 55 and the handle 52 and the EFP probe 30 is exposed to the fluid 14, and wherein the EFP probe 30 has a known length.

Providing an electrical pulse emitter 120 that electronically generates an electrical pulse and which is delivered to the EFP probe 30 via a coaxial cable 75, and wherein the electrical pulse travels the length of the EFP probe 30, and subsequently generates an electrical pulse reflection.

Providing an electrical pulse sampler 150 electronically coupled with the EFP probe 30 by means of coaxial cable 75, and which further receives, and senses, the electrical pulse reflection generated by electrical pulse within the EFP probe 30.

Providing a controller/computer electronically coupled with the temperature probe, the EFP probe, the electrical pulse emitter, the electrical pulse sampler, and the database, and wherein the controller/computer determines a time period between the electrical pulse emission into the EFP probe, and the receipt of the sensed electrical pulse reflection from the EFP probe, and wherein resonance points of the fluid are calculated by the controller/computer from the electrical pulse reflection by applying a Fast Fourier Transform algorithm to the electrical pulse reflection, and wherein scattering parameters S11 and S21 are calculated by the controller/computer from the electrical pulse reflection by applying a Fast Fourier Transform algorithm to the electrical pulse reflection, and wherein the complex permittivity curve of the fluid oil and water mixture is calculated by the controller/computer from scattering parameters S11 and S21, and wherein the controller/computer further correlates the determined time period and the determined resonance points and the calculated complex permittivity curve to the previously determined, and known, complex permittivity curves of the volume fraction of water, and the volume fraction of oil as provided in the database, and as adjusted for temperature to identify the volume fraction of water, and the volume fraction of oil in the fluid thereby allowing the computer to determine an oil/water ratio of the fluid.

Providing a density probe having an elongate support with a handle end, and an opposing distal end, and wherein the elongate support carries a first pressure transducer which is located proximate to the handle end and which is exposed to the fluid, and a second pressure transducer is located at the distal end, opposite the handle end is simultaneously exposed to the fluid, and wherein a known predetermined distance is established between the first pressure transducer, and the second pressure transducer.

Operationally coupling the controller with the first pressure transducer and the second pressure transducer, and determining a pressure differential between the first pressure transducer and the second pressure transducer so as to calculate the density of the fluid based upon the identified volume fraction of water, and the identified volume fraction of oil as adjusted for temperature as previously provided by the temperature probe.

Providing a user interface electronically coupled with the controller/computer, and which receives the measurement of the oil water ratio, and the density of the fluid, and which further generates a user perceivable output which identifies the oil water ratio and the density of the fluid.

Therefore, it will be seen that the present invention provides a convenient method whereby a user may determine and measure multiple parameters of a fluid, with more particularity, a drilling fluid, in a manner not possible, heretofore.

In compliance with the statute, the invention has been described in language more or less specific as to the structural and methodical features. It is to be understood, however, that the invention is not limited to the specific features shown or described since the means herein disclose comprised preferred forms of putting the invention into effect. The invention, is therefore, claimed in any of its forms or modifications, within the proper scope of the appended claims, appropriately interpreted in accordance with the doctrine of equivalents.

We claim:

1. A method for measuring multiple parameters of fluid comprising:
    providing a source of fluid providing a fluid having a volume fraction of water and a volume fraction of oil, and wherein the volume fraction of water and the volume fraction of oil each have a previously determined and known dielectric constant, previously determined and known resonance points and a complex permittivity curve;
    providing a database having stored accessible information about the previously determined and known dielectric constants, previously determined and known resonance points of various concentrations and complex permittivity curves of the volume fractions of water and of oil;
    providing a temperature probe exposed to the fluid to determine the temperature of the fluid;
    providing an Electric Field Perturbation (EFP) probe exposed to the fluid, and wherein the EFP probe has a known length;
    providing an electrical pulse emitter that electronically generates an electrical pulse and which is delivered to the EFP probe, and wherein the electrical pulse travels the length of the EFP probe, and subsequently generates an electrical pulse reflection when encountering a change in impedance;
    providing an electrical pulse sampler electronically coupled with the EFP probe, and which further receives, and senses, the electrical pulse reflection, and which further receives, and senses, the electrical pulse transmitted through the EFP probe;
    providing a controller/computer electronically coupled with the temperature probe, the EFP probe, the electrical pulse emitter, the electrical pulse sampler, a density probe and the database, and wherein the controller/computer determines a time period between the electrical pulse emission into the EFP probe, and the receipt of the sensed electrical pulse reflection from the EFP probe, and wherein resonance points of the fluid are calculated by the controller/computer from the electrical pulse reflection and transmission by applying a Fast Fourier Transform (FFT) algorithm to the electrical pulse reflection and transmission, and wherein scattering parameters S11 and S21 are calculated by the controller/computer from the electrical pulse reflection and transmission by applying a Fast Fourier Transform (FFT) algorithm to the electrical pulse reflection and transmission, and wherein a calculated complex permittivity curve of the fluid mixture is calculated by the controller/computer from the scattering parameters S11 and S21, and wherein the controller/computer further correlates the determined time period and the determined resonance points and the calculated complex permittivity curve of the fluid mixture to the previously determined, and known, complex permittivity curves of the volume fraction of water, and the volume fraction of oil as provided in the database, and as adjusted for temperature to identify the volume fraction of water, and the volume fraction of oil in the fluid thereby allowing the controller/computer to determine an oil/water ratio of the fluid;
    providing a density probe having an elongate support with a handle end, and an opposing distal end, and wherein the elongate support carries a first pressure transducer which is located proximate to the handle end and which is immersed in the fluid, and a second pressure transducer is located at the distal end opposite the handle and is simultaneously immersed in the fluid, and wherein a known predetermined distance is established between the first pressure transducer, and the second pressure transducer;
    operationally coupling the controller/computer with the first pressure transducer and with the second pressure transducer, and determining a pressure differential between the first pressure transducer and the second pressure transducer so as to calculate the density of the fluid based upon the identified volume fraction of water, and the identified volume fraction of oil as adjusted for temperature as previously provided by the temperature probe; and
    providing a user interface visual display electronically coupled with the controller/computer, and which receives the determined measurement of the oil-water ratio, and the density of the fluid, and which further generates a user perceivable output which identifies the oil-water ratio and the density of the fluid.

2. A method for measuring multiple parameters of fluid of claim 1 and wherein the EFP Probe has a generally planar metallic body having a first end and an opposing second end, a first edge and an opposing second edge, a first surface and an opposing second surface with a thickness between the first surface and the second surface, and a chrome alumina oxide coating extending entirely about the body;
 an elongated gap defined by the body generally medially between the first edge and the second edge, the elongated gap communicating with an end of the body;
 a first ground plate defined by the body between the first edge and a proximate edge of the elongated gap, the first ground plate structurally attached to the body proximate the first end and extending toward the second end;
 a second ground plate defined by the body between the second edge and a proximate edge of the elongated gap, the second ground plate structurally attached to the body proximate the first end and extending toward the second end; and
 an elongate center conductor within the elongated gap and extending parallel to and between the first ground plate and the second ground plate, the center conductor having an end portion terminating within the elongated gap between the first ground plate and the second ground plate.

3. A method for measuring multiple parameters of fluid of claim 1 and wherein the fluid is drilling fluid.

4. A method for measuring multiple parameters of fluid of claim 1 and wherein the EFP probe is portable.

5. A method for measuring multiple parameters of fluid of claim 1 and wherein the density probe is portable.

6. A method for measuring multiple parameters of fluid of claim 1 and wherein the EFP probe is interconnected to a pipe communicating with the source of fluid so that the EFP probe is at least partially exposed to the fluid in the pipe.

7. A method for measuring multiple parameters of fluid of claim 1 and wherein the fluid that is being measured is contained in a reservoir/tank.

8. A method for measuring multiple parameters of fluid comprising:
 providing a source of fluid that provides a fluid having volume fractions, and wherein the volume fractions each have a previously determined and known dielectric constant, previously determined and know resonance points and a previously determined and known complex permittivity curve;
 providing a database having stored accessible information about the previously determined and known dielectric constants, previously determined and known resonance points of various concentrations of the volume fractions and previously determined and known complex permittivity curves of the volume fractions;
 providing a temperature probe exposed to the fluid to determine the temperature of the fluid;
 providing a density probe having a first pressure transducer and a second pressure transducer that are spaced apart by a known distance and which are simultaneously immersed in the fluid;
 providing an Electric Field Perturbation (EFP) probe immersed in the fluid, and wherein the EFP probe has a known length;
 providing an electrical pulse emitter that electronically generates an electrical pulse and which is delivered to the EFP probe, and wherein the electrical pulse travels along the length of the EFP probe, and subsequently generates an electrical pulse reflection when the electrical pulse encounters a change in impedance;
 providing an electrical pulse sampler electronically coupled with the EFP probe, and which further receives, and senses, the electrical pulse reflection;
 providing a controller/computer electronically coupled with the temperature probe, the EFP probe, the electrical pulse emitter, the electrical pulse sampler, the density probe and the database;
 performing, with the controller/computer, a time domain evaluation of the fluid and correlating the time domain evaluation results to the previously determined and known dielectric constants and resonance points and complex permittivity curves stored in the database to identify the volume fraction constituents of the fluid;
 performing, with the controller/computer, a frequency domain evaluation of the time domain evaluation results by performing a Fast Fourier Transform of the time domain evaluation results to generate a sine wave and further perform a Power Spectral Density calculation of the sine wave to determine a frequency and amplitude of the sine wave to identify resonance points of the fluid, and correlating the identified resonance points of the fluid to the previously determined and known resonance points of volume fractions stored in the database; and
 providing a user interface electronically coupled with the controller/computer, and which further generates a user perceivable output which identifies the oil-water ratio and the density of the fluid.

9. A method for measuring multiple parameters of fluid of claim 8 and further comprising:
 calculating, with the controller/computer, scattering parameters S11 and S21 from the electrical pulse reflection and transmission, and
 calculating, with the controller/computer, a calculated complex permittivity curve of the fluid mixture from the scattering parameters S11 and S21; and
 correlating, with the controller/computer, the determined time period and the determined resonance points and the calculated complex permittivity curve to the previously determined, and known, complex permittivity curves of the volume fractions as provided in the database, and as adjusted for temperature to identify the volume fractions in the fluid.

10. A method for measuring multiple parameters of fluid of claim 8 and wherein the fluid is drilling fluid.

11. A method for measuring multiple parameters of fluid of claim 8 and wherein the EFP probe is portable.

12. A method for measuring multiple parameters of fluid of claim 8 and wherein the density probe is portable.

13. A method for measuring multiple parameters of fluid of of claim 8 and wherein the EFP probe is interconnected to a pipe communicating with the source of fluid so that the EFP probe is at least partially exposed to the fluid in the pipe.

14. A method for measuring multiple parameters of fluid of claim 8 and wherein, the fluid that is being measured is contained in a reservoir/tank.

* * * * *

UNITED STATES PATENT AND TRADEMARK OFFICE
CERTIFICATE OF CORRECTION

| | |
|---|---|
| PATENT NO. | : 11,549,910 B2 |
| APPLICATION NO. | : 16/615078 |
| DATED | : January 10, 2023 |
| INVENTOR(S) | : Mohr et al. |

It is certified that error appears in the above-identified patent and that said Letters Patent is hereby corrected as shown below:

In the Specification

Column 13: Line 47: Insert the number --18-- after the number 14.

In the Claims

Column 29: Line 47: Delete the word "know" and insert the word --known--.

Column 30: Line 50: Delete the word "of", as it is listed twice.

Signed and Sealed this
Twentieth Day of February, 2024

*Katherine Kelly Vidal*

Katherine Kelly Vidal
*Director of the United States Patent and Trademark Office*